United States Patent [19]
Augustine et al.

[11] Patent Number: 5,807,332
[45] Date of Patent: Sep. 15, 1998

[54] TUBE APPARATUS FOR WARMING INTRAVENOUS FLUIDS WITHIN AN AIR HOSE

[75] Inventors: Scott D. Augustine, Bloomington; Randall C. Arnold, Minnetonka, both of Minn.

[73] Assignee: Augustine Medical, Inc., Eden Prairie, Minn.

[21] Appl. No.: 658,698

[22] Filed: Jun. 5, 1996

Related U.S. Application Data

[63] Continuation-in-part of Ser. No. 216,139, Mar. 22, 1994, abandoned.

[51] Int. Cl.$^6$ .................................................. A61F 7/12
[52] U.S. Cl. ...................... 604/113; 165/163; 285/401; 285/402; 607/104
[58] Field of Search .................... 604/113, 114; 607/96, 104, 105–107; 165/163; 285/401, 402

[56] References Cited

U.S. PATENT DOCUMENTS

| | | | |
|---|---|---|---|
| 1,493,450 | 5/1924 | Richardson . | |
| 1,995,302 | 3/1935 | Goldstein | 128/254 |
| 2,507,464 | 5/1950 | De Andrade So | 219/39 |
| 3,551,641 | 12/1970 | Truhan . | |
| 3,968,346 | 7/1976 | Cooksley | 219/305 |
| 4,167,663 | 9/1979 | Granzow, Jr. et al. | 219/497 |
| 4,214,147 | 7/1980 | Kraver | 219/301 |
| 4,281,238 | 7/1981 | Noma et al. | 219/535 |
| 4,293,762 | 10/1981 | Ogawa | 219/302 |
| 4,306,018 | 12/1981 | Kirkpatrick | 435/2 |
| 4,347,894 | 9/1982 | Gerlach | 165/76 |
| 4,384,578 | 5/1983 | Winkler | 604/114 |
| 4,532,414 | 7/1985 | Shah et al. | 219/308 |
| 4,653,577 | 3/1987 | Noda | 165/71 |
| 4,709,135 | 11/1987 | Dietrich et al. | 219/303 |
| 4,734,269 | 3/1988 | Clarke et al. | 422/310 |
| 4,759,749 | 7/1988 | Verkaart | 604/113 |
| 4,772,778 | 9/1988 | Ogawa | 219/30 |
| 4,787,883 | 11/1988 | Kroyer | 604/4 |
| 4,796,696 | 1/1989 | Stocton et al. | 165/169 |
| 4,833,299 | 5/1989 | Estes | 219/311 |
| 4,878,537 | 11/1989 | Verkaart | 165/156 |
| 4,895,203 | 1/1990 | Metanen | 165/41 |
| 4,900,308 | 2/1990 | Verkaart | 604/126 |
| 4,908,014 | 3/1990 | Kroyer | 604/4 |
| 5,063,994 | 11/1991 | Verkaart | 165/154 |
| 5,073,167 | 12/1991 | Carr et al. | 604/114 |
| 5,074,838 | 12/1991 | Kroyer | 604/4 |
| 5,077,980 | 1/1992 | Weher | 62/130 |
| 5,097,898 | 3/1992 | Verkaart | 165/154 |
| 5,106,373 | 4/1992 | Augustine et al. | 604/113 |
| 5,165,472 | 11/1992 | Cloutier | 165/159 |
| 5,228,505 | 7/1993 | Dempsey | 165/140 |
| 5,245,693 | 9/1993 | Ford et al. | 392/470 |
| 5,254,094 | 10/1993 | Starkey et al. | 604/113 |
| 5,269,749 | 12/1993 | Koturov | 604/4 |
| 5,271,085 | 12/1993 | Carballo | 392/444 |
| 5,379,832 | 1/1995 | Dempsey | 165/110 |
| 5,474,538 | 12/1995 | Stihler et al. | 604/113 |
| 5,522,871 | 6/1996 | Sternlicht | 607/107 |
| 5,588,968 | 12/1996 | Sternlicht | 607/107 |

FOREIGN PATENT DOCUMENTS 0172480  2/1986  European Pat. Off. .

*Primary Examiner*—Corrine M. McDermott
*Assistant Examiner*—Cris L. Rodriguez
*Attorney, Agent, or Firm*—Gray Cary Ware & Freidenrich

[57] ABSTRACT

An IV fluid warmer that utilizes a warmed airstream supplied through an air hose to heat IV fluid flowing through one or more helically coiled warming tubes positioned within the air hose. In one embodiment, support unit keeps the one or more warming tubes in the air hose, exposed to the warmed airflow. A nozzle provided on the distal end of the air hose has an outer housing and an inner ring slidably positioned therein. The outer housing includes an outer slot and the slidable inner ring includes an inner slot. When aligned, the support unit can be inserted through the inner and outer slots and the inner ring may be rotated to lock the support unit into position within the air hose. In another embodiment, helically coiled warming tube is self-supporting within the air hose. The IV fluid warmer can achieve high heating rates and low flow resistance in this configuration. Furthermore, it can utilize an airstream source of heat such as that conventionally used with inflatable thermal blankets.

25 Claims, 14 Drawing Sheets

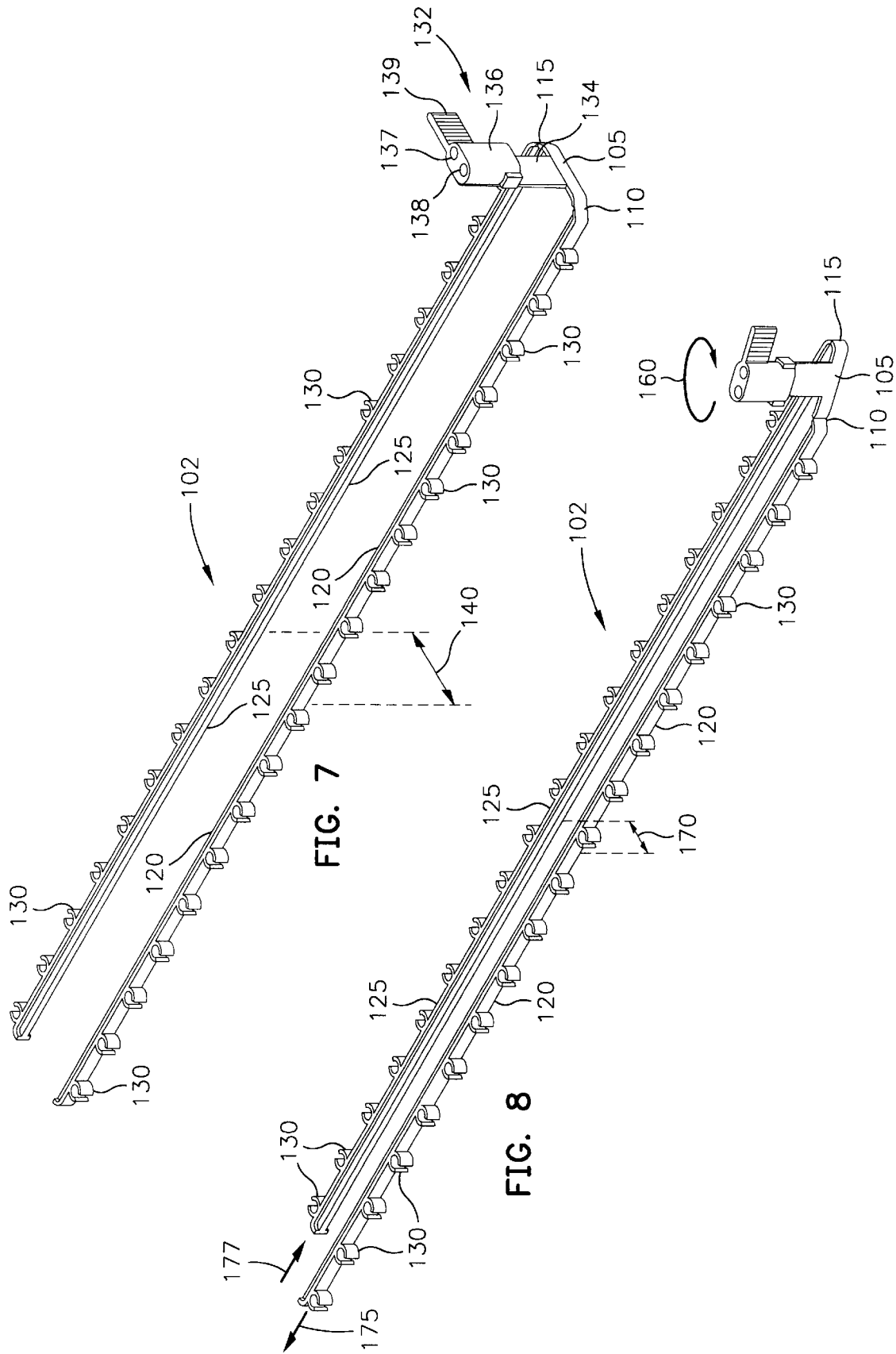

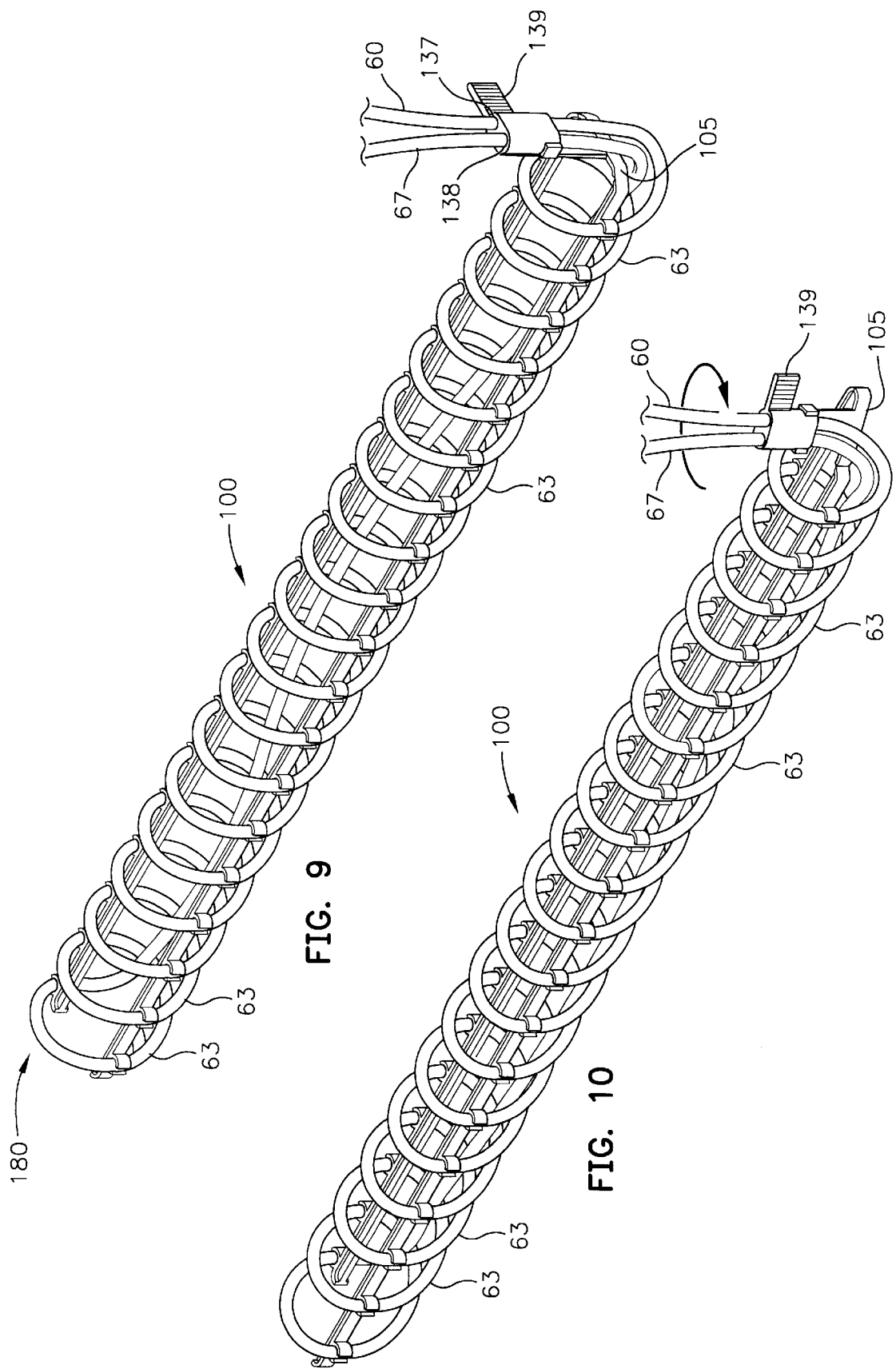

TUBE APPARATUS FOR WARMING INTRAVENOUS FLUIDS WITHIN AN AIR HOSE

This application is a continuation-in-part (CIP) of Pat. application Ser. No. 08/216,139, filed Mar. 22, 1994, now abandoned, entitled "INTRAVENOUS FLUID WARMING METHOD AND APPARATUS," which is expressly incorporated by reference herein.

BACKGROUND OF THE INVENTION

1. Field of the Invention

This invention relates to intravenous administration of fluids to a patient, and particularly relates to the efficient warming of such fluids while they are being intravenously administered to a patient.

2. Description of the Related Art

Fluids that are administered intravenously to a patient include blood-based fluids and non-blood fluids, collectively referred to as "IV fluids" herein. While awaiting use, blood-based fluids are maintained in cool storage at approximately 4° C. Non-blood fluids are usually stored at room-temperature.

It is well known that hypothermia poses a significant peril to emergency patients and to surgical patients during or after surgery. Intravenous administration of unheated IV fluids in such patients can cause substantial heat loss and can cause, or at least contribute to, serious patient hypothermia problems, especially with cooler fluids.

In the art, it is known to warm IV fluids prior to intravenous administration. However, care must be exercised: overheating IV fluids, especially blood-based compositions, could destroy cells. It has been recognized that convection is a very safe method for warming IV fluids because there is a reduced risk of overheating when a gas such as heated air is used to transfer thermal energy, rather than a liquid. Examples of convection systems for heating IV fluids are disclosed in U.S. Pat. No. 4,707,587 and U.S. Pat. No. 5,106,373.

U.S. Pat. No. 4,707,587 discloses a blood warming method using air as a heating medium. This patent discloses a structure that warms blood by flowing it through a blood warming jacket that includes a serpentine path through which the blood is circulated. The blood is heated by conductive contact with an airflow apparatus. Unfortunately, the jacket is quite bulky and cumbersome and provides a lengthy path for the blood to flow, which creates a high flow resistance that renders the device incapable of handling medium and higher flow rates of blood at 4° C.

U.S. Pat. No. 5,106,373, assigned to the assignee of this present application and incorporated herein by reference, discloses placing IV fluids in a warming location over which heated gas flows. Furthermore, U.S. Pat. No. 5,106,373 discloses that the heated gas could be used to simultaneously operate a patient warming blanket, such as the warming blankets disclosed in U.S. Pat. Nos. 4,572,188, 5,300,102 and 5,324,320, all assigned to the assignee of this application and incorporated by reference herein.

The parent application, Ser. No. 08/216,139, which is assigned to the assignee of this present application, provides a convenient method and apparatus for quickly heating an IV fluid for delivery to a patient, while reducing the risk of over-heating. The IV fluid warming system in Ser. No. 08/216,139 includes an inlet tube connected to an IV fluid source and a heated gas source in communication with a warming conduit. The inlet tube is connected to an inlet manifold that has a single port for receiving the inlet tube and a plurality of ports for receiving a plurality of warming tubes. A support structure holds the plurality of warming tubes in a parallel configuration extending outwardly from the manifold, looping around and then returning the plurality of tubes again in a parallel configuration to an outlet manifold that has a plurality of ports for receiving the plurality of warming tubes and a single port for receiving an outlet tube. The outlet tube is used to transport warmed IV fluid to the patient. The warming tube and support structure are positioned within the warming conduit so that heated air convectively warms the IV fluid flowing through the warming tubes. An airflow coupler is used in conjunction with the warming conduit to couple the apparatus to a warming blanket. The airflow coupler provides a locking mechanism to removably secure the warming tube in place. The multi-tube design advantageously creates a large cross-sectional area of fluid exposed to air within a conventional heated air conduit, and the airflow coupler provides a firm mechanism for positioning the IV tube within the heated air conduit.

The intravenous fluid warming apparatus described in the above-referenced 5,106,373 patent and the 08/216,139 application has received general approval: the fluid warmer efficiently and effectively warms fluids prior to administration to patients. However, certain enhancements are still useful in order to realize additional clinical objectives and to enjoy further advantages in its use. Particularly, there is a possibility to improve the invention described in the incorporated patent application 08/216,139 to aid in ease of insertion into the heated air conduit. The IV warming system may be further improved by reducing the amount of tubing in the warming loop, by eliminating the need for a manifold system, and by simplifying the procedure for purging air emboli. It is also useful to retain the ability to remove the warming tube for repairs and replacement.

SUMMARY OF THE INVENTION

An IV fluid warmer is disclosed herein that can achieve high heating rates and low flow resistance. The IV fluid warmer utilizes a source of warmed air that is supplied through an air hose connected to the source at its proximal end. A nozzle is mounted on the distal end of the air hose through which warmed air flows. The nozzle is adapted to be received in an inlet port of an inflatable thermal blanket. An IV heating tube is provided that includes an inlet tubing segment connected to the IV fluid source, an outlet tubing segment for transporting IV fluid to the patient, and one or more warming tube segments connected between the inlet and outlet segments. A support structure holds the one or more warming tube segments in a warming configuration. The support structure is retained in the nozzle such that the one or more warming tube segments are positioned within the air hose whereupon the warming segments are bathed and heated by the flow of warmed air. The invention warms IV fluid during delivery to a patient from a source of IV fluid.

In the embodiment of the incorporated patent application, an inlet tube is connected to the fluid source for transporting the IV fluid. The inlet tube is splayed into a one or more warming tubes by a first manifold. An air hose is placed in communication with a heater/blower assembly. The one or more warming tubes are placed into the air hose and then rejoined into an outlet tube by a second manifold. The outlet tube transports warmed IV fluid to the patient. Airflow coupling means are used in conjunction with the air hose for coupling the first embodiment apparatus to a nozzle on the air hose through which the warmed air is supplied. The airflow coupling means provides a locking mechanism to removably secure the warming tube support structure in place on the nozzle.

In a first embodiment of this invention, at least a portion of at least one helically coiled warming tube segment is positioned in an air hose. The warming tube segment may be supported within the air hose, or it may be self supporting. In the first regard a support unit keeps a helically coiled warming tube segment in the air hose. The support unit permits the warming tube segment to be rotated between an open configuration in which the helically coiled warming tube segments is extended (i.e., "opened") and a collapsed configuration in which coils of the helical configuration are closely positioned and the coils are flattened. In the collapsed configuration, the helically coiled warming tube and the support unit can be easily inserted into an air hose through which a warmed airstream flows. In its opened configuration within the air hose, the helically coiled warming tube exposes the coils to the flow of warmed air to allow more effective heating of the IV fluid flowing through the coiled warming tube.

A nozzle is provided on the air hose with provision for keeping the helically coiled warming tube in the air hose. For the first embodiment, the nozzle also includes a collar for attaching to an air inlet port of a conventional inflatable thermal blanket. Alternatively, an adaptor, receivable on the end of the nozzle is provided for attachment. An airflow restrictor may be attached to the collar to provide sufficient pressure for effective heating of the IV fluid within the conduit.

The embodiment of the IV fluid warmer with the helically disposed warming tube segments achieves high heating rates and high flow rates by coiling the warming tube and positioning the coils horizontally in the heated-air conduit so that the tubing presents a perpendicular profile to the airflow through the conduit. This configuration takes advantage of the physical principle that heat transfer from air to any object is significantly more efficient if the angle of impingement is near 90°. The efficiency advantage provided by the substantially perpendicular air-tubing contact surface can provide the same total heat transfer to the IV fluids as the first embodiment warming apparatus (disclosed in Ser. No. 08/216,139) with less surface area and hence less total tubing requirements, which advantageously has a smaller priming volume, lower cost to manufacture and ease of insertion into the hose. In summary, the substantially perpendicular orientation of the coiled tube creates a significantly more efficient fluid warming device that has lower cost and provides higher flow rates.

In both embodiments the nozzle has a dual purpose. First, it provides a simply operated, pluggable coupling with an air inlet port of an inflatable thermal blanket, where it directs a warmed airflow into the blanket. Second, it keeps the support unit and the one or more warming tubes within the warmed airflow in order that the fluid flowing in the one or more warming tubes is warmed.

The invention therefore also extends to an air hose nozzle that performs at least two functions: (1) coupling a warmed airstream to an inflatable thermal blanket, and (2) keeping an IV tube structure in the warmed airstream for the purpose of warming the IV fluid. Relatedly, the nozzle has a side opening and a mechanism that engages an IV structure and keeps the IV structure in the warmed airstream. The inventors contemplate that an air hose with the nozzle may be part of a warmed airflow source for use with inflatable thermal blankets in which the air hose is attached to a heater/blower assembly.

Moreover, the inventors contemplate that the invention covers an IV tube support structure with an engagement mechanism that engages an air hose nozzle for seating and retaining the structure in the nozzle, whereat the structure may position one or more warming tubes in a warmed air stream.

In accordance with the objectives of this invention as described above and to overcome the limitations of the prior art, the foregoing, together with other objects, features and advantages of this invention, will become more apparent when referring to the following specification, claims and the accompanying drawings.

BRIEF DESCRIPTION OF THE DRAWINGS

For a more complete understanding of this invention, reference is now made to the following detailed description of the embodiments as illustrated in the accompanying drawings, wherein:

FIG. 2 is a cutaway view of an air hose showing a support structure that positions multiple IV tube loops in a warmed air stream, FIG. 3 shows a manifold apparatus, FIG. 4 shows a perspective view of an air hose nozzle having a mechanism for engaging the manifold apparatus of FIG. 3, with the mechanism in a partially open unlocked position, and FIG. 5 shows, from the same perspective of FIG. 4, the mechanism in a closed, locked position;

FIG. 7 is a perspective view of a support unit for the coiled warming tube in an open configuration.

FIG. 8 is a perspective view of the support unit in a closed configuration.

FIG. 9 is a perspective view of a coiled tube assembly including the support unit and coiled warming tube in an open configuration.

FIG. 10 is a perspective view of the coiled tube assembly in a closed configuration.

DETAILED DESCRIPTION OF THE PREFERRED EMBODIMENTS

This invention is described in preferred embodiments in the following description with reference to the Figures, in which like numbers represent the same or similar elements. While this invention is described in terms of specific embodiments for achieving manifold objectives, it will be appreciated by those skilled in the art that variations may be accomplished in view of these teachings without deviating from the spirit or scope of the invention.

Figure 1:
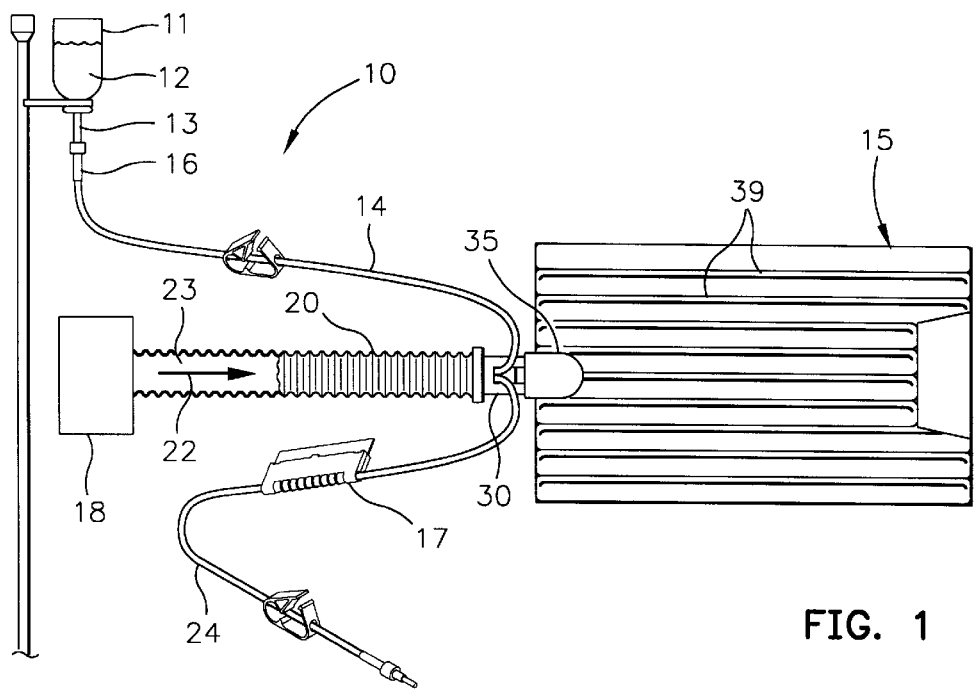
FIG. 1 is a perspective view of an embodiment of the heating apparatus in which an IV fluid warming apparatus is disposed in an air hose used to inflate an inflatable thermal blanket with warmed air.

FIG. 1 illustrates an apparatus 10 for warming an IV fluid 12 during delivery through an IV delivery tube 14 to a patient (not shown) while simultaneously warming the patient with a conventional inflatable thermal blanket 15 such as that described in detail in the incorporated U.S. Pat. No. 5,324,320. As is known, the thermal blanket 15 controls the patient's body temperature by convective warming, using pressurized, heated air supplied by a source 18. The source 18 may include a heater/blower assembly that warms air and generates a warmed air stream. The inflatable thermal blanket 15 is connected by a flexible conduit (e.g., a flexible air hose) 20 to source 18, which forces a warmed airstream 22 through a central bore 23 in the air hose 20 in which a warming tube support structure is positioned. The flexible air hose 20 is connected through an airflow coupling (also, "nozzle") 30 to the blanket 15 at inlet port 35. Inflatable chambers 39 in the blanket are inflated with heated air, as described in the '320 patent. The heated air 22 inflates the blanket 15 in the manner described in the incorporated '320 patent, and flows out of apertures in the underside of the blanket to warm the patient.

In conjunction with FIG. 1, reference is now made to FIGS. 2–5 in which an embodiment of the invention is illustrated. An important aspect of this embodiment includes a means for splaying the inlet tube 14 such that cross-sectional and surface areas of the fluid 12 are increased. Such an increase may be accomplished by splaying the tube 14 into a plurality of warming tubes 28 such that the plurality of warming tubes may be placed through an opening 25 of the air hose 20 and into the central bore 23. This increases the surface area of the fluid and the cross-sectional area through which the IV fluid flows, thus increasing the dwell time of the fluid in the warmed airstream and the amount of heat transferred through the tubes 28 to the fluid. The increased cross-sectional area also reduces resistance to the flow of the IV fluid. The inventors envision that other means for increasing the cross-sectional area and surface area of this fluid may be used, based on the teachings herein, including the use of a single warming tube instead of a plurality of warming tubes. The plurality of warming tubes 28 are held together by band 27, forming a warming loop 31. The loop 31 is formed as warming tubes 28 turn direction at turn 29 which directs the fluid into an outlet tube 24. The outlet tube may be attached to a needle (not shown) for delivery of warmed IV fluid to a patient (not shown). Clamps may used to control the flow of the IV fluid by opening and closing tubes. A temperature indicator 17 shown on the outlet tube 24 allows for monitoring temperature of the warmed IV fluid.

Figure 2:
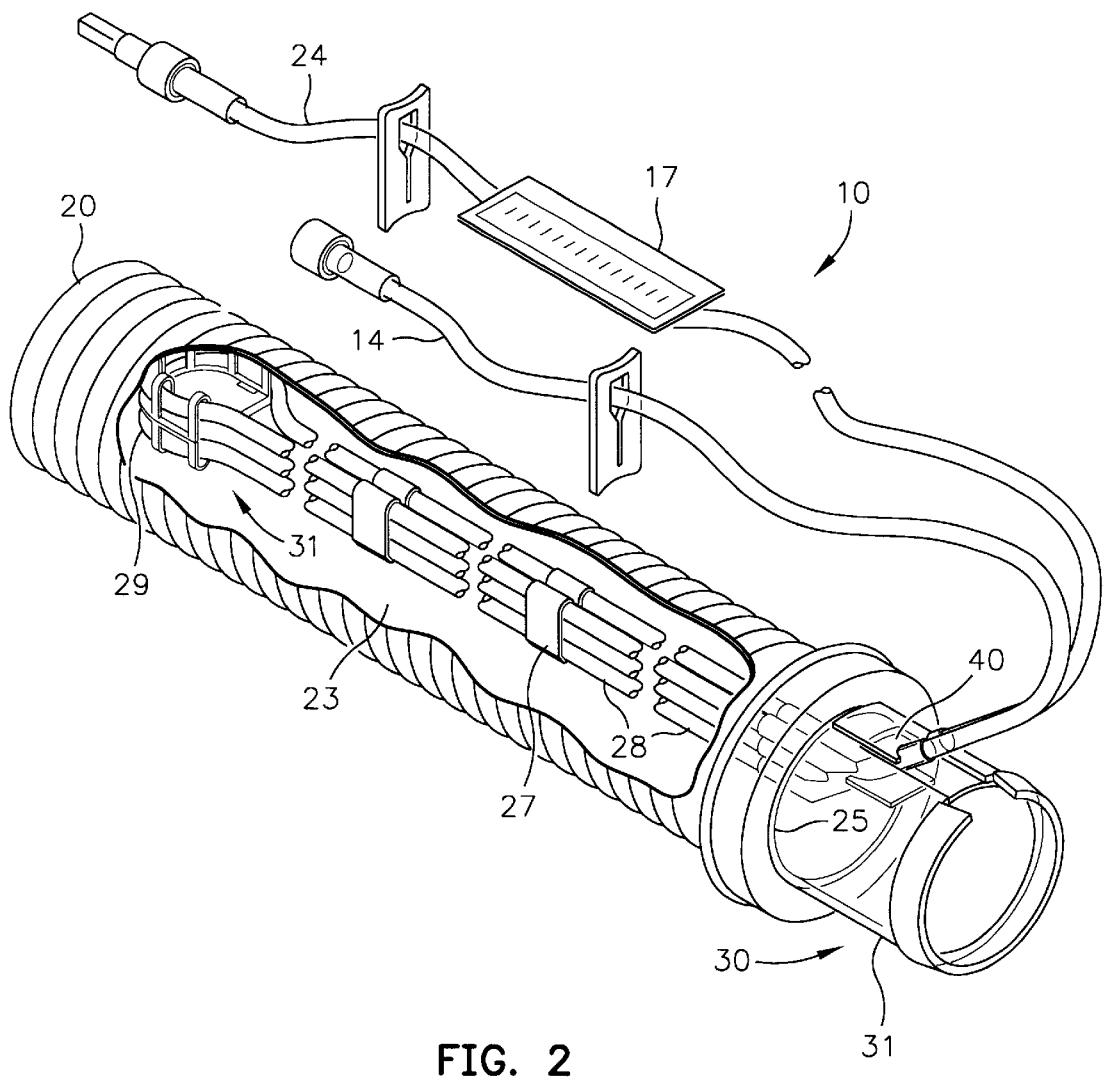
FIGS. 2–5 illustrate the embodiment of the invention in the incorporated patent application, where
Figure 3:
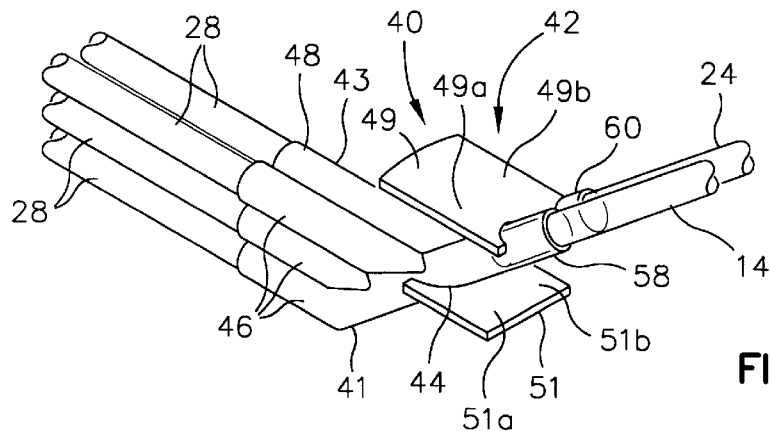

Referring to FIGS. 2 and 3, the splaying of the inlet tube 14 into a plurality of warming tubes 28 is accomplished by a manifold block 40. The manifold block includes a first manifold 41 having a port 44 in fluid communication with a plurality of ports 46. The first manifold 41 is used in the invention to splay the inlet tube 14 into the tubes 28. The manifold block 40 also includes a second manifold 43 for joining the plurality of warming tubes 28 to the outlet tube 24. The second manifold 43 includes a plurality of ports 48 in fluid communication with the single port 45. Thus, fluid communication from the source of IV fluid 12 through the tube 14, the first manifold 41, the plurality of warming tubes 28, the second manifold 43, and outlet 24 accomplishes an affective method of heating an IV fluid while simultaneously inflating an inflatable thermal blanket to reduce the risk of hypothermia in a patient.

An engagement means 42 on the manifold block 40 slidably engages the manifold block to nozzle 30 with the warming tubes 28 disposed within the air hose 20. This results in the inlet tube 14 and outlet tube 24 being outside the air hose and accomplishes warming while separating the fluid flow into areas which may be regulated by clamps and measured by the temperature sensor 17.

Figure 4:
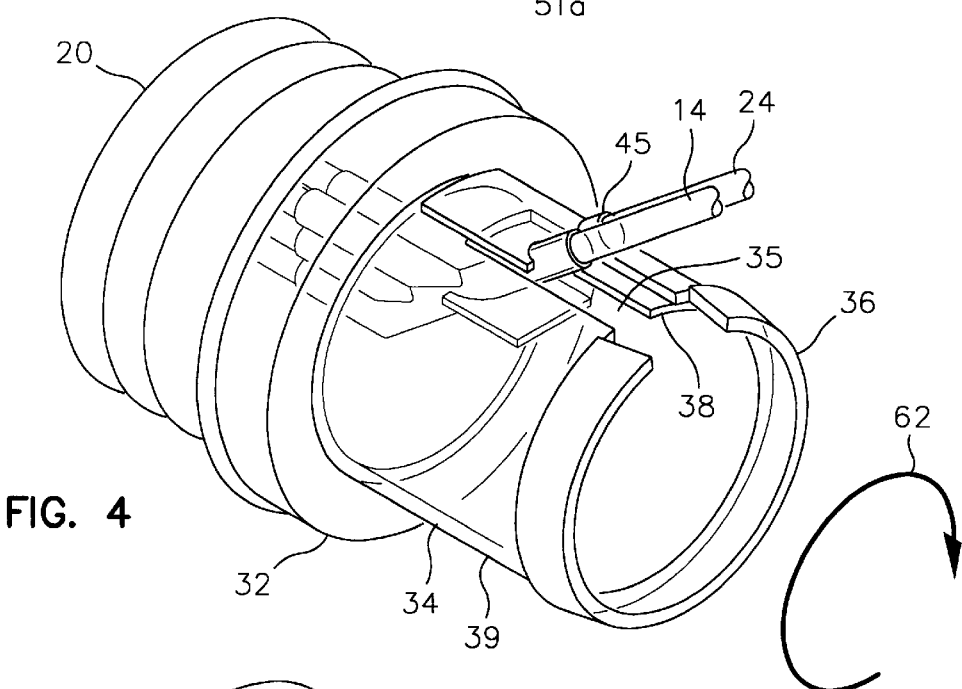
Figure 5:
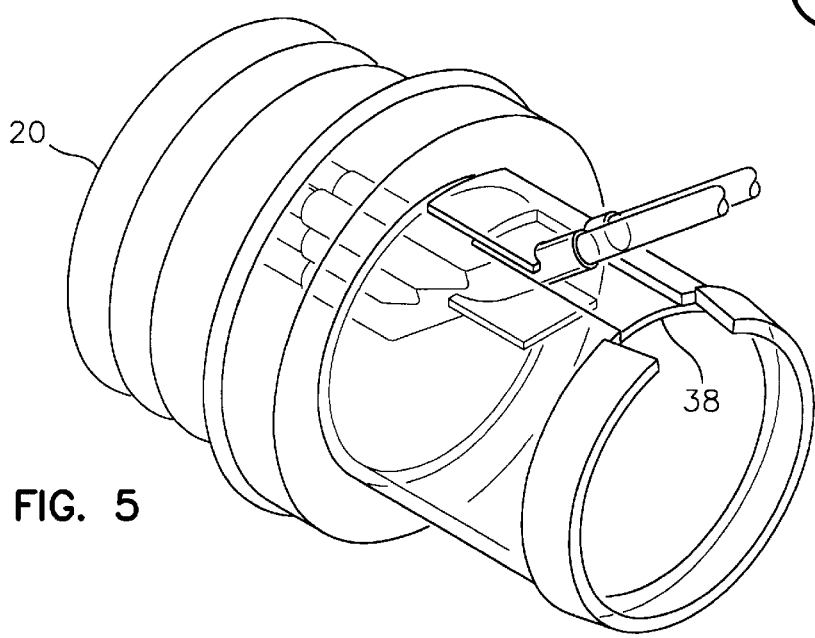

Referring to FIGS. 2, 3, 4, and 5, the nozzle 30 is shown attached to an end of the flexible air hose 20. The nozzle may have a forward section 31 with a right cylindrical or frustoconical shape. In the first embodiment, a slot 35 is provided inside of the forward section 31 of the nozzle 30. An engagement means 42 on the manifold block 40 slidably engages the slot such that an inlet port 58 connected to the tube 14, and an outlet port 60 connected to the outlet tube 24 are disposed outside the air hose 20. The plurality of warming tubes 28 and their respective couplings are disposed within the air hose 20. The nozzle 30 includes a shallow collar section 32 to attach to a first end of the air hose and an elongate tubular section 34 formed integral with the shallow collar section. The nozzle further includes a collar 36 rotatably mounted on the elongate tubular section 34 for rotating to a first position and opening slot 35, and rotating to a second position closing the slot 35 to retain the manifold block 40. In the first embodiment, the engagement means 42 comprises a first plate 49 forming a pair of planar extensions 49a and 49b mounted on the first side of the manifold block 40, and a second plate 51 forming a pair of planar extensions 51a and 51b mounted on a second side of manifold block 40 in opposition to the first set of planar extensions. Thus, each set of planar extensions forms a recess for engaging a respective side of the slot 35. The nozzle 30 includes an inner ring 38 and an outer ring 39. When the collar 36 is rotated, the inner ring 38 formed integral with collar 36, also rotates. FIG. 4 shows the slot partially opened. When collar 36 is rotated in direction 62, slot 35 closes behind the manifold block 40 as shown in FIG. 5, retaining the manifold block in the slot 35. Thus, the plurality of warming tubes 28 connected to the manifold block are held in a fixed position securely in the air hose. This insures safety for patient by preventing inadvertent dislodging of the IV warming apparatus.

In the helically disposed embodiment of the IV fluid warming apparatus, as illustrated in FIGS. 6–17, a single, helically-coiled tube is placed in the warmed airstream and is kept there by a support structure which, like the manifold block 40 couples to and seats in the nozzle 30. Alternatively, the helically coiled structure may be self-supporting, as described later in detail.

Figure 6:
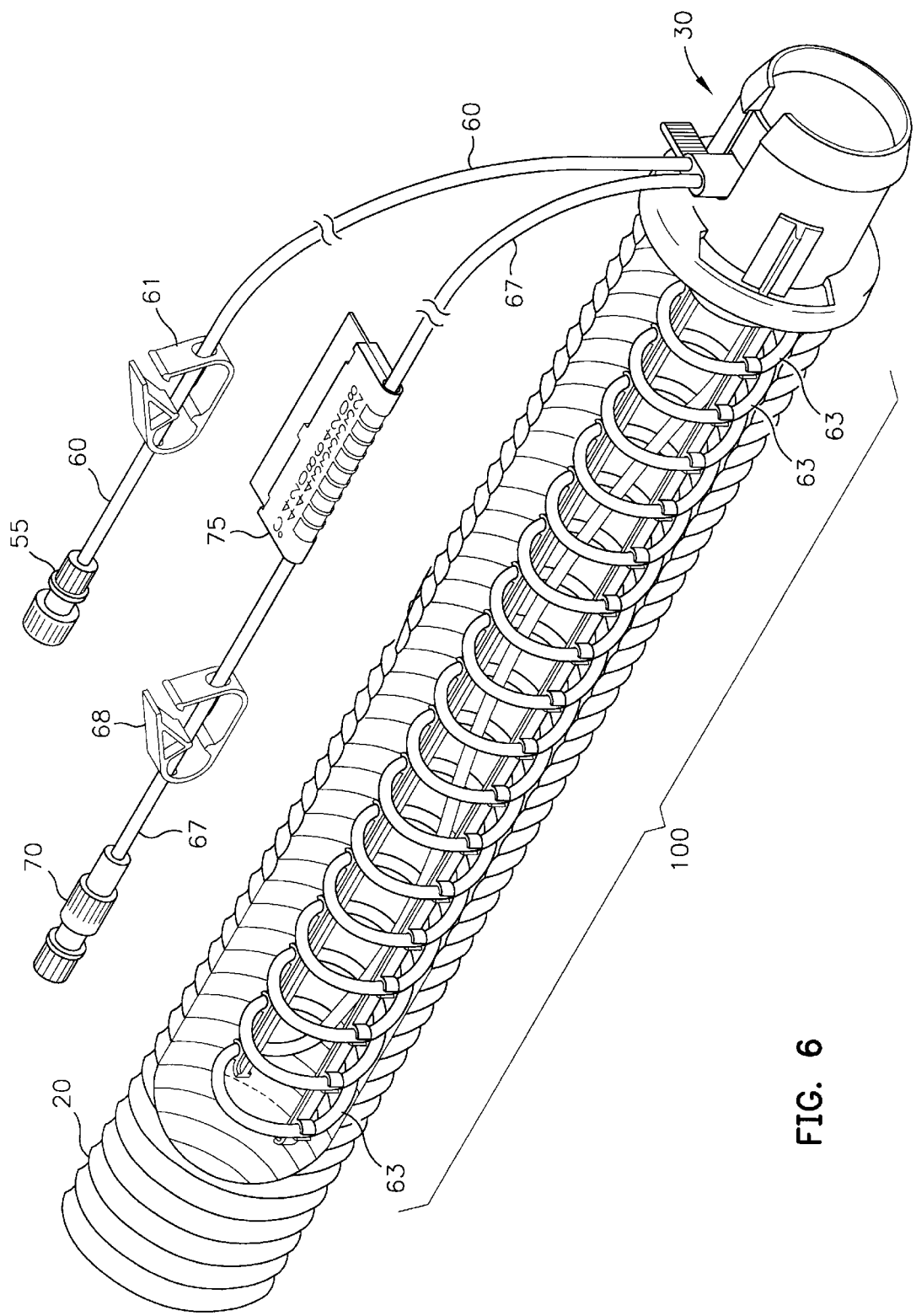
FIG. 6 is a perspective view of an air hose with a section cut away to reveal an embodiment of this invention, which includes a coiled tube assembly situated therein. The figure further shows the inlet tubing segment, the outlet tubing segment, and a temperature indicator positioned on the outlet tubing segment.
Figure 18:
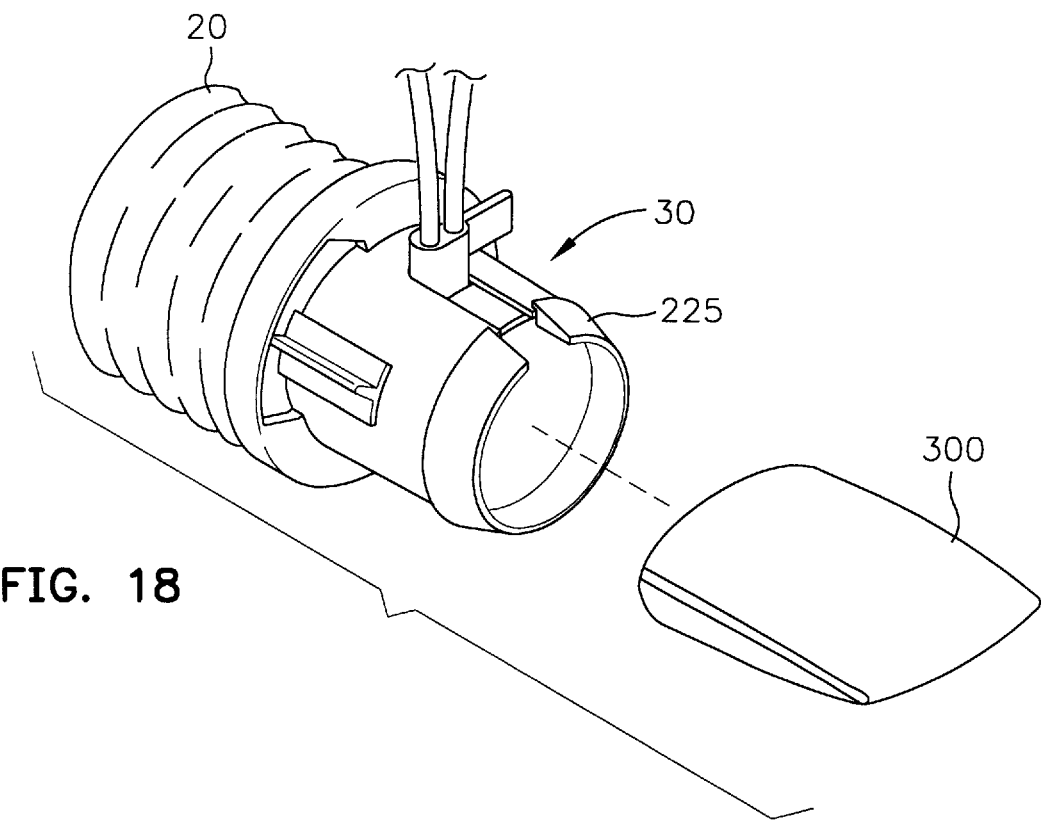
FIG. 18 is a perspective view of an airflow restrictor to be inserted over the outer cylindrical housing of the nozzle.

In conjunction with FIG. 1, reference is now made to FIG. 6, which is a perspective view of the air hose 20 with a section cut away to reveal a helically coiled tube assembly 100 situated therein. FIG. 1 shows that the IV fluid 12 is delivered from the IV bottle 11 through the IV delivery tube 13 that on its other end is connected via a conventional screw-type coupler 16 to the inlet tube 14. An inlet segment 60 delivers the IV fluid 12 to a helically coiled warming segment 63, which delivers warmed IV fluid to an outlet segment 67 that, in turn, provides the heated IV fluid to a patient. A conventional push-type tube clamp 61 is positioned on the inlet segment 60, and a conventional push-type tube clamp 68 is positioned on the outlet segment 67 to removably block fluid flow. A conventional screw-type coupler 70 is attached to the outlet side of the outlet segment 67 in order to facilitate connection with an additional tube and an IV needle (not shown) that administers the heated IV fluid to the patient. A temperature indicator 75, preferably comprising a sheet of thermochromic material, is attached to the outlet segment 67 to measure the temperature of the heated IV fluid exiting from the coiled segment. Preferred embodiments of the temperature sensor 75 are shown in FIGS. 18, et seq., and described in detail in connection therewith.

The heating tube collectively comprises the inlet segment 60, the helically coiled warming segment 63, and the outlet segment 67, which preferably are respective sections of a single piece of tubing, thereby reducing cost and also reducing the possibility of leakage over previous multi-tube designs. However, design considerations may dictate that these sections be physically separate. As used herein, a "tube" is merely a fluid channel for transporting the fluid from a source to a patient. Generally, any form or shape of fluid channel will suffice; however, a tube is a convenient choice.

The warming apparatus 10 includes the source 18, the air hose 20 in communication with the source, and the coiled tube assembly 100 disposed therein. The coiled tube assembly 100 includes the coiled segment 63 and a support unit 102 that provides a structure for supporting the coiled section. The coiled tube assembly 100 can easily shift between a collapsed configuration suitable for insertion or removal, and an open configuration suitable for IV fluid warming.

Reference is now made to FIGS. 7, 8, 9 to describe the coiled tube assembly 100 of the second embodiment. FIGS. 7 and 8 show the support unit 102 in two different configurations: FIG. 7 shows a first, open configuration and FIG. 8 shows a second, collapsed configuration.

The support unit 102 includes a transverse member 105 comprising a substantially rigid middle section. A first flexible hinge 110 is provided on one end of the transverse member and a second flexible hinge 115 is provided on the other end. A first elongated rib 120 is coupled to the first hinge 110 and a second elongated rib 125 is coupled to the second hinge 115. Preferably the elongated ribs 120 and 125 comprise a semirigid material such as plastic. Examples of suitable plastic materials include polypropylene (PP), polyvinyl chloride (PVC) or polyethylene (P/E). In the second embodiment, the first and second ribs, the first and second hinge, and the transverse member are formed of a single piece of plastic. In this second embodiment, the hinge mechanism in the hinged spacer segment is preferably an integrally molded "living hinge".

The first and second ribs include a plurality of clasping notches 130 spaced evenly along their outward facing edges to provide a clasping means for the tubing that coils around them. Each of the clasping notches 130 include a pair of cupped members having a size and shape for removably affixing tubing that has a shape predetermined by the tubing in the coiled segment 63 of the heating tube. The transverse member 105 is connected to an insertion lever shown generally at 132 that allows easy manipulation and furthermore locks the warming device into a retaining slot provided in the heated-air conduit. The insertion lever 132 includes a flat support tab 134 connected along the transverse member 105. The support tab 134 is connected to a retaining clip 136 that has a through hole 137 and a through slot or channel 138 formed extending therethrough, each having a size to allow passage of the warming tube. Particularly, the through hole 137 is used to pass (and anchor) the inlet segment 60, and the through channel 138 is used to pass (and anchor) the outlet segment 67. A thumb tab 139 is connected to the retaining clip to facilitate manipulation and rotation of the transverse member 105 in order to shift between a first, open configuration and a second, collapsed configuration, as described in detail herein. Preferably, the support tab 134, the retaining clip 136, and the thumb tab 139 are integrally molded together in one piece of plastic material together with the transverse member 105 and the entire support unit 102.

The hinged transverse member 105 advantageously allows the substantially parallel ribs 120 and 125 to easily shift between a first configuration (FIG. 7) in which the ribs are fully separated for efficient heating during operation, and a second configuration (FIG. 8) in which the side combs are folded together to facilitate insertion into the heating conduit and allow removal therefrom subsequent to use. In other words, the second configuration creates a substantially flattened structure. FIG. 7 shows the support unit 102 in an open configuration in which the first and second ribs have an approximately perpendicular relationship to the transverse member 105. In this open configuration, the first rib 120 is separated from the second rib 125 by a distance 140 that is directly related (although not necessarily equal) to the length of the transverse member 105. In FIG. 7 the first rib 120 has a substantially parallel relationship with the second rib 125, which is their preferred orientation when the coiled tube section 63 is snapped (i.e. inserted) into the clasping notches 130, as shown in FIG. 9.

Although the second embodiment has only one hinge (at the proximal end), other embodiments (not shown) may include regularly spaced hinged supports at intervals along the midline, oriented perpendicularly to the ribs in order to maintain a substantially fixed relationship between the first rib 120 and the second rib 125. These other embodiments may include a hinged spacer segment located at the distal end of the spine. However, for increased flexibility and low cost of manufacture, the additional hinged segments are eliminated in the preferred embodiment. In the open configuration of the preferred embodiment the tube coil exerts forces axially outward that force the first and second ribs apart throughout their entire length, therefore eliminating the requirement for additional spacers.

FIG. 8 is a perspective view of the support unit 102 in the second, collapsed configuration in which the transverse member 105 has been twisted in the rotational direction shown by the arrow 160, while maintaining the substantially parallel orientation of the first rib 120 and the second rib 125. In the resultant collapsed configuration, the first rib is separated from the second rib by a second distance 170 that is substantially less than the distance 140 of the open configuration. Furthermore, the first rib and the second rib are shifted longitudinally with respect to each other. Particularly, the first rib is shifted in a distal direction shown by an arrow 175 and the second rib is shifted in the reverse direction shown by a second arrow 177. Thus, in the collapsed configuration, the first and second ribs occupy less space than in the open configuration, and as will be seen with reference to FIG. 10, for example, the relative shifting of the first and second ribs substantially flattens the coiled tube section, with the result that the overall coiled tube assembly is flattened which has advantages including easy insertion and removal from the heated-air conduit in which it is situated.

FIG. 9 is a perspective view of the first, open configuration of the coiled tube assembly 100, which includes the support unit 102 on which the coiled tube section 63 has been affixed into the clasping notches 130. Preferably each of the plurality of tubing loops in the coil are affixed so that each loop has a substantially identical diameter, and therefore the coil is symmetrical throughout its length. The inlet segment 60 passes through the inlet through hole 137 in the insertion lever 132 and begins looping around the first and second ribs until the coil is complete at a distal end 180. The remaining tubing is passed through the center of the coil and exits via the outlet through channel 138.

In the open configuration of FIG. 9, the loops in the coiled tube section are fully extended, which situates them perpendicular to the airflow in the heated-air conduit and allows for effective heating. FIG. 10 is a perspective view of the second, open configuration of the coiled tube assembly 100. In comparison with FIG. 9, the collapsed configuration in FIG. 10 shows the loops substantially flattened due to the longitudinal shifting of the first and second ribs, as well as their relative closeness. The collapsed configuration allows easy insertion into the heated-air conduit 20.

Figure 11:
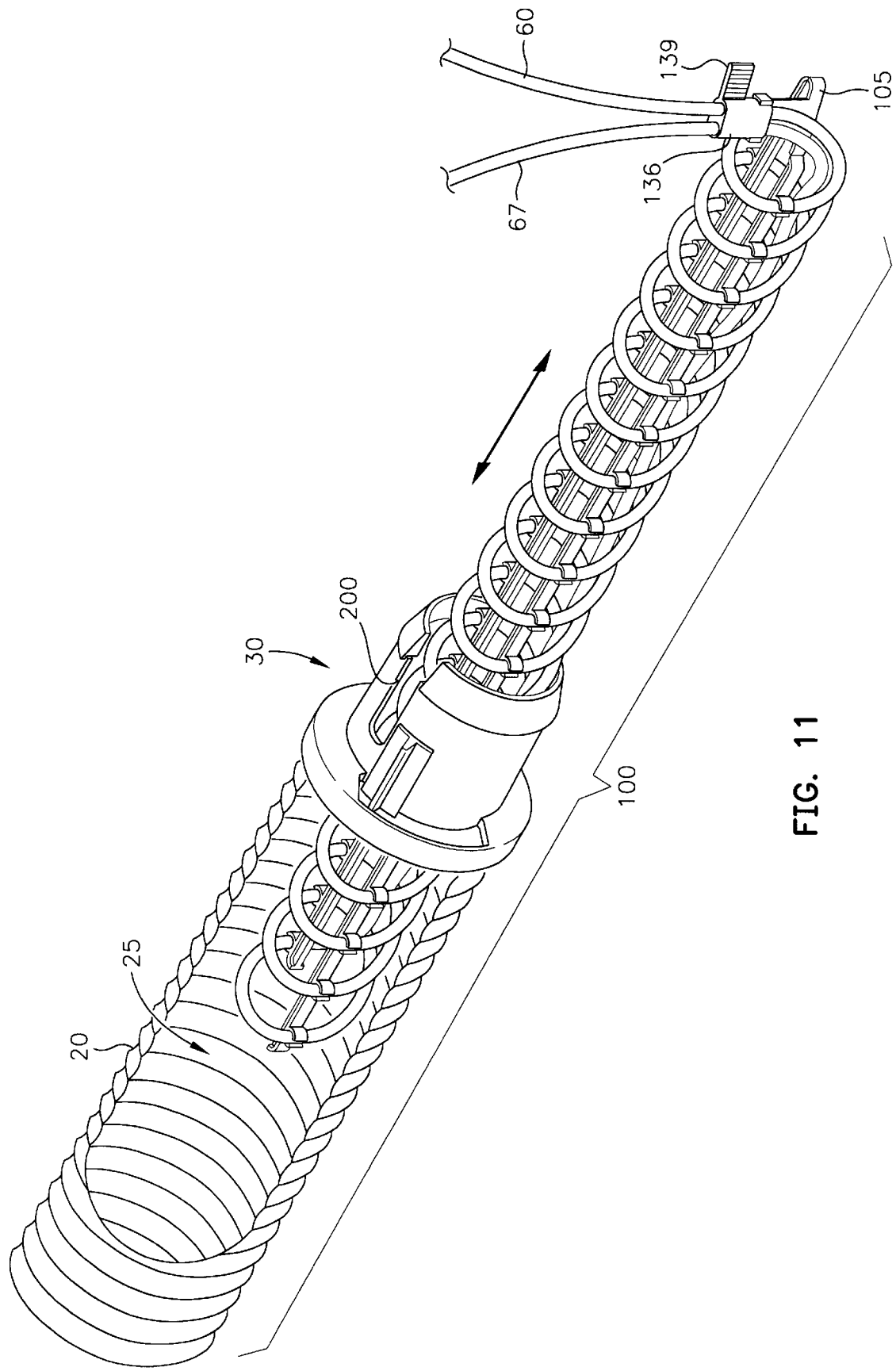
FIG. 11 is a perspective view of the coiled tube assembly being inserted into a heated-air conduit with a section cut away to reveal the coiled tube assembly within the air conduit.

FIG. 11 is a perspective view of the air hose 20 with a section cut away to reveal the helically coiled tube assembly 100 being inserted through the nozzle 30 into the central bore 23. For insertion or removal, such as illustrated in FIG. 11, the coiled tube assembly 100 is in its collapsed configuration which utilizes minimal space and facilitates easy insertion. To place the coiled tube assembly 100 in its collapsed configuration, the thumb tab 139 can be utilized to manipulate and rotate the transverse element 105 to provide the illustrated configuration. As will be described in more detail subsequently with reference to FIGS. 11, 16 and 17, for example, the retaining clip 136 is inserted into a longitudinally-formed slot that is formed in the nozzle 30.

Figure 12:
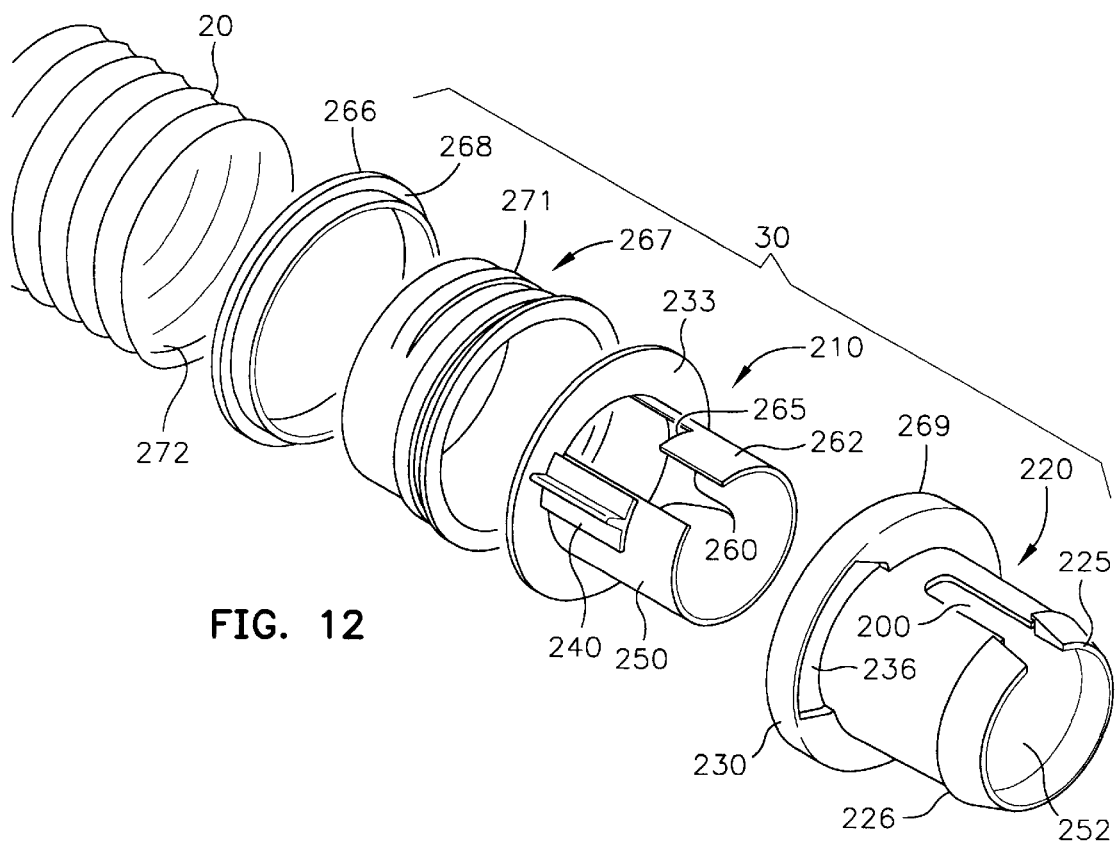
FIG. 12 is a perspective, exploded view of the nozzle showing an outer cylindrical housing and an inner cylindrical member.

Reference is now made to FIGS. 12, 13, 14, and 15 to describe the nozzle 30 in detail. FIG. 12 is a perspective, exploded view of the nozzle 30, comprising an cutaway cylindrical member 210 and an outer cylindrical housing 220. The outer housing 220, which has another slot 200 formed longitudinally therein, also includes an outer collar 225 having an annular shape on the end distal from the air hose 20. Preferably, the collar 225 has an annular notch 226 for coupling with an inflatable thermal blanket (FIG. 1). The outer housing 220 also includes, on its end proximate to the air hose 20, a coupling collar 230 having a shape for coupling with the air hose 20 and slidably engaging with a flat annular surface 233 provided on the inner cylindrical member 210. The hose coupling collar 230 also includes an access slot 236 formed facing toward the distal end of the outer housing 220. The access slot 236 has a shape for accommodating a lever 240 extending from the flat annular surface 233, which allows a user to rotate the inner ring within the outer housing.

The inner cylindrical member 210 includes a cylindrical section 250 having a diameter for inserting slidably within an inner diameter 252 of the outer housing 220 so that said inner member and said outer housing have a slidable, rotatable relationship. The inner member 210 includes an axially-formed inner slot 260, a locking tab 262 adjacent to the inner slot and a locking slot 265 formed between the tab 262 and the flat annular surface 233. When aligned, the inner slot 260 and the outer slot 200 of the outer housing allow passage of the retaining clip 136 on the coiled tube assembly 100.

The nozzle is assembled by containment of the inner cylindrical member 210 between the outer cylindrical housing 220 and a ring 266. A threaded cylindrical piece 267 is also held between the housing 220 and the ring 266. To assemble the nozzle, the cylindrical section 250 of the inner cylindrical member is inserted into the inner diameter 252 and the threaded cylindrical piece 267 is brought against the back of the flat annular surface 233. The ring 266 is then placed over the threaded portion 271 of the threaded cylindrical piece 267 and brought against the back of the coupling collar 230 so that the surface 268 faces an annular surface (not shown, but indicated by 269) of the collar 230. The surfaces 268 and 269 are bonded by any conventional means, with the threaded cylindrical piece and the inner cylindrical member 210 being rotatably held between the housing 220 and ring 226. The nozzle is coupled to the air hose 20 by rotating the threaded cylindrical piece 267 within the air hose 20 so that the threaded portion engages the inner surface 272 of the air hose 20.

Figure 13:
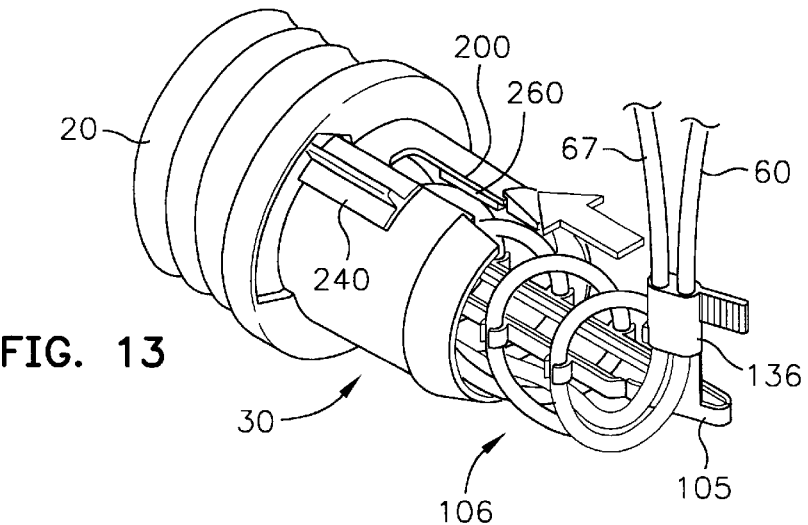
FIG. 13 is a perspective view of an assembled nozzle in an open position in which the inner slot of the inner ring is aligned with the outer slot in the outer housing so that the coiled tube assembly can be inserted therein.

FIG. 13 illustrates an assembled nozzle 30 in the open position in which the movable lever 240 is positioned so that the inner slot 260 of the inner cylindrical member is aligned with the outer slot 200. In this open position, the coiled tube assembly 100 can be easily accommodated therein, as also shown in FIG. 11.

Figure 14:
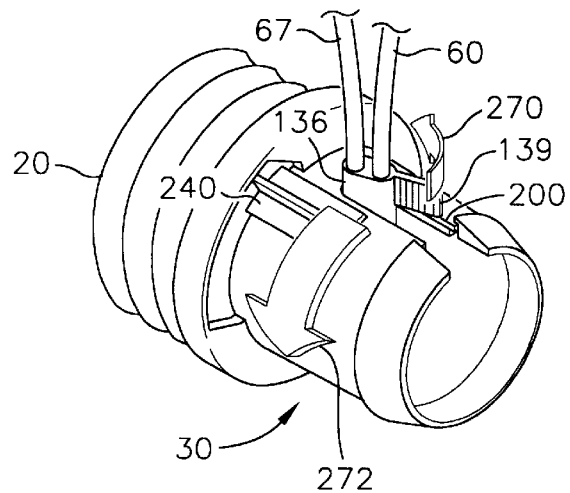
FIG. 14 is a perspective view of the coiled tube assembly fully inserted through the nozzle, with the coiled tube assembly still being in the collapsed configuration.

FIG. 14 is a perspective view of the coiled tube assembly 100 inserted into the nozzle 30 in a collapsed configuration. As part of insertion, the retaining clip 136 is fully inserted into the outer slot 200. FIG. 14 shows a fully inserted configuration prior to locking. To lock the coiled tube assembly, the thumb tab 139 is manipulated in the direction of the arrow 270 and the lever 240 is moved in the direction of the arrow 272 in order to lock the coil tube assembly 100 into position, as illustrated in FIG. 15.

Figure 15:
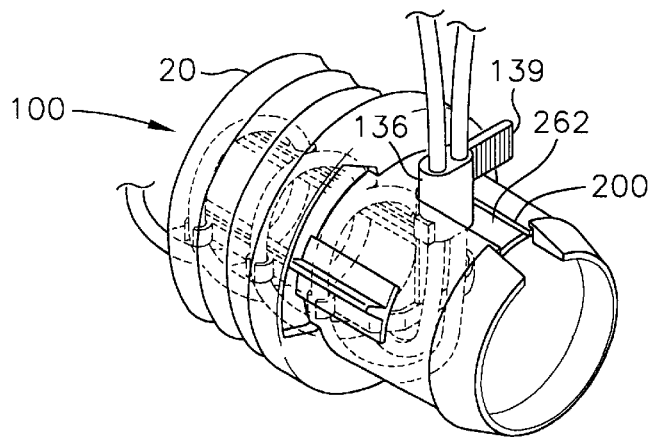
FIG. 15 illustrates the coiled tube assembly locked into position within the air hose, with the coiled tube assembly in the open configuration for effective heating.

FIG. 15 illustrates the coiled tube assembly 100 locked into position within the air hose 20. The retaining clip 136 has been rotated by, for example, the thumb clip 139 so that it is positioned at the end of the outer slot 200 and is held in place, in the open configuration, by the locking tab 262 formed on the inner annular member. In this position, the coiled tube assembly 100 is fully inserted and locked into position. In this configuration, the nozzle is ready to be inserted into the thermal blanket 15, or if appropriate, an airflow restrictor 300, as described below and illustrated in FIGS. 18 and 19, can be utilized.

Figure 16:
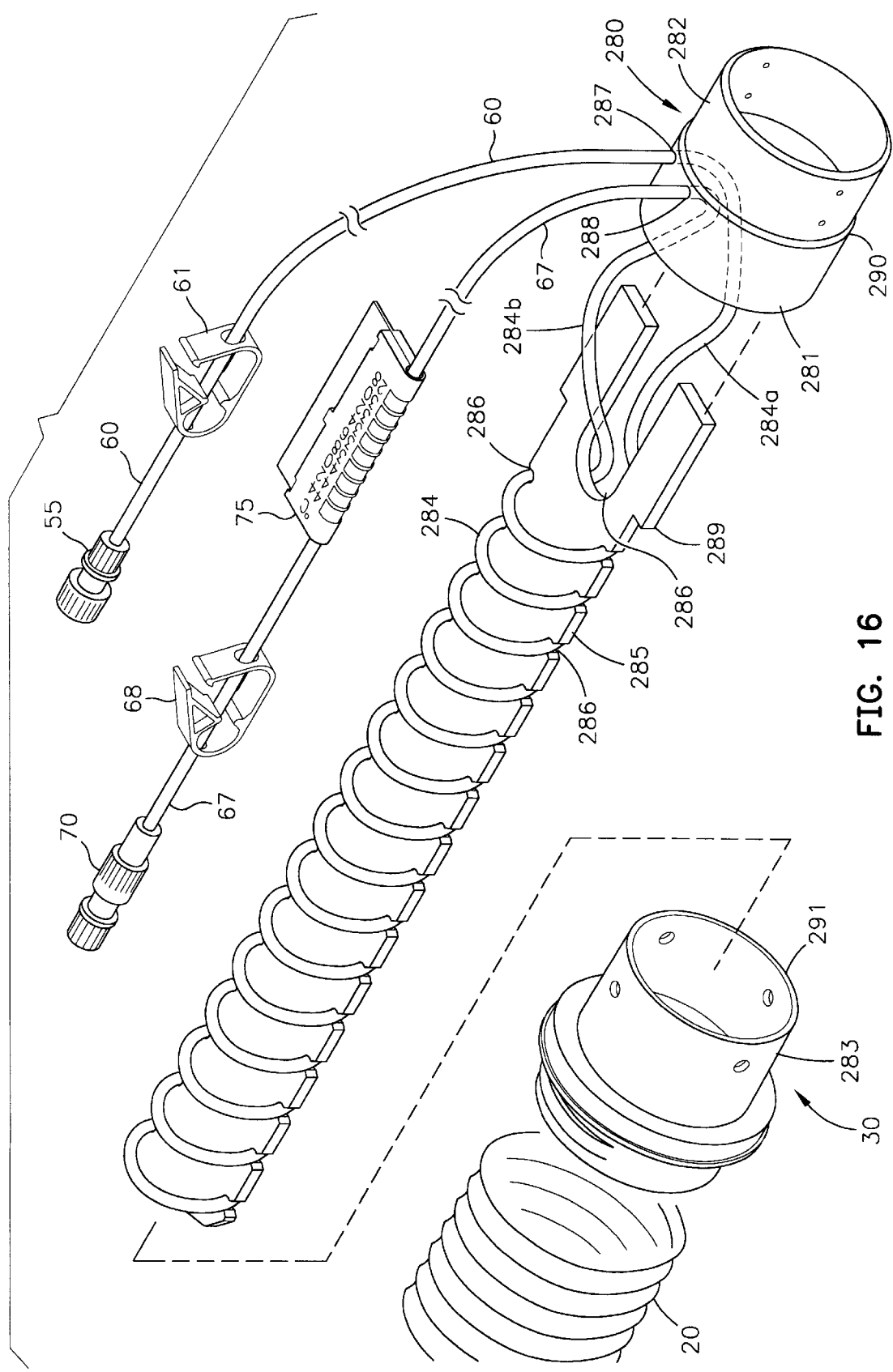
FIG. 16 shows an alternate embodiment of the support structure.
Figure 17:
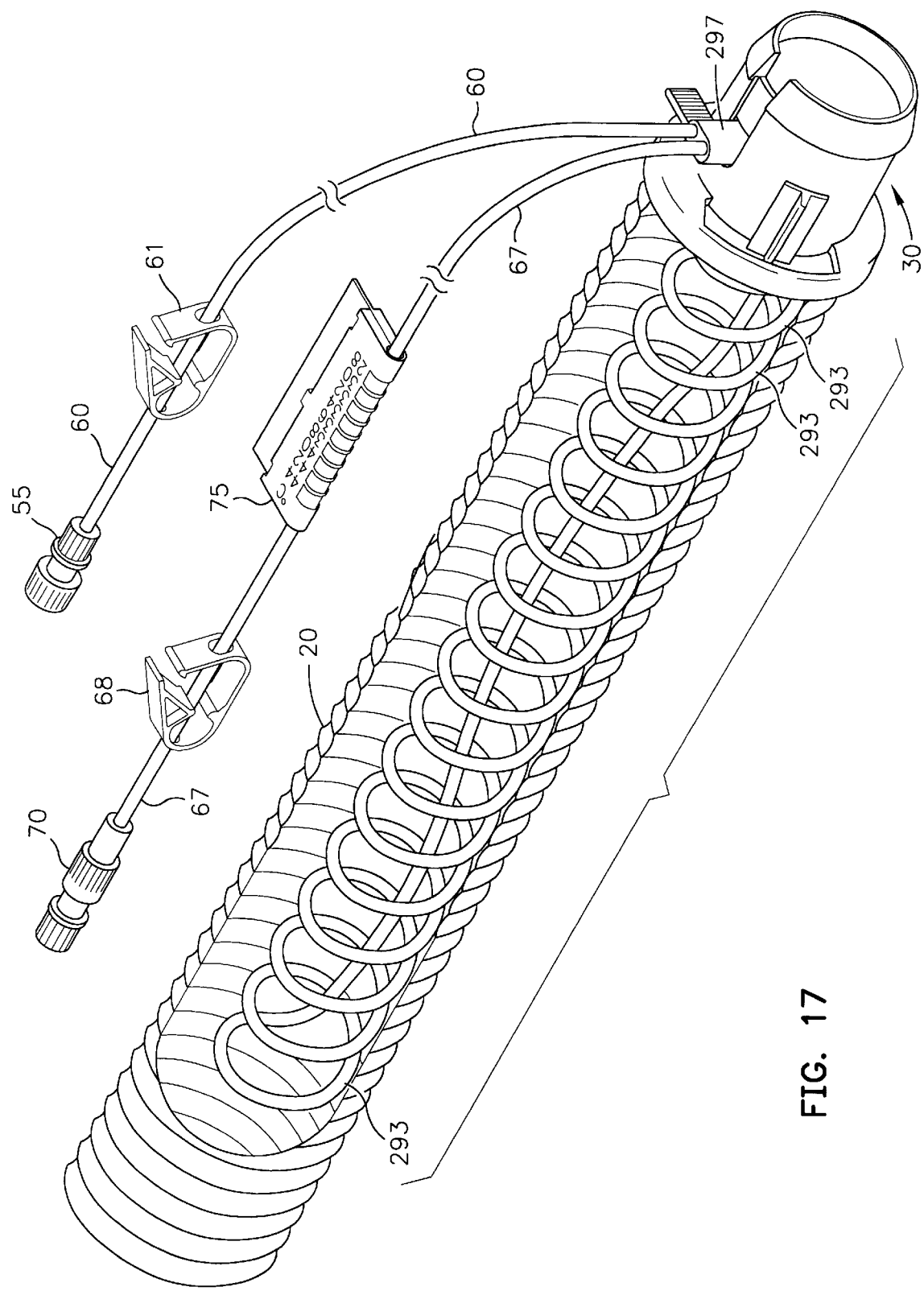
FIG. 17 shows a helically coiled warming tube segment.

FIGS. 16 and 17 illustrate another embodiment for positioning a warming tube section in an air hose for convectively warming fluid while operating an inflatable thermal blanket. The arrangement of FIG. 16 includes the air hose 20 and the nozzle 30 together with an adapter 280 that has a cylindrical section with a first relatively large diameter at 281 and a second somewhat smaller diameter at 282. The diameter at 282 is equal to the diameter of the forward section 283 of the nozzle 30. However the diameter 281 is large enough to fit over the forward portion of the nozzle 30 (which has the diameter 283). This permits mounting of a warming tube section 284 within the air hose 20 by insertion through the nozzle 30. In this regard, the warming tube section 284 is helically coiled on an elongate support piece 285 having notches 286 therein for receiving and retaining coils of the warming tube section 284. The support piece 285 is preferably a hard plastic piece with a large notch 286 having a curved end for receiving and retaining warming tube section portions 284a and 284b. Portions 284a and 284b extend through holes 287 and 288, respectively, were they join, or transition to, the inlet and outlet tubes 60 and 67. The support piece 285 in its forward portion that includes the curved notch 286 transitions at 289 from a first width to a second, relatively broader width. The broader width at the end of the support piece 285 is slightly smaller than the diameter 281 of the adapter piece 280. This permits the forward end of the support piece 285 to be slidably inserted into the adapter piece 280 in the larger diameter portion 281, wherein it is stopped by the transition 290 from the diameter 281 to the diameter 282 and were it is retained by, for example, ultrasonic or glue bonding. Thus assembled, the support piece 285 is inserted into the nozzle 30 through the diameter portion 283 until the outer annular surface 291 is stopped against the width transition 289. Preferably, the interior of section 281 and the outer surface of the forward section 283 are tapered about 1° to provide a positive connection between the interior surface of the section 281 and the outer surface of the forward section 283. This permits the nozzle and retainer piece 280 assembled and disassembled as required for clinical use.

FIG. 17 illustrates retention of a coiled warming tube segment 293 within the air hose 20 without any support structure. Preferably the warming tube section 293 is formed from the same material as the input and output sections 60 and 67, but with a higher durometer so that the section 293 has enough stiffness to retain its coiled shape during handling and retention in the air hose 20. The warming tube section 293 is coupled to the input and output tubes 60 and 67 and retained in the nozzle 30 by a retainer 297 having the structure and general operation disclosed above with respect to retaining clip 136 shown in FIGS. 7 and 8. Of course, the retainer 297 is not connected at its lower extremity to a support structure as is the retaining clip 136. However, the retainer 297 provides holes through which the inlet and outlet sections 60 and 67 extend and a structure that permits removable retention of the warming tube section 293 within the air hose 20 by slidable engagement with a nozzle 30 as described above.

FIG. 18 is a perspective view of an airflow restrictor 300 to be used with the nozzle 30 in which the coiled tube assembly 100 has been fully inserted and locked into place. In order to provide sufficient backflow pressure for effective heating of the IV fluid that will be flowing within the coiled tube assembly, the airflow restrictor 300 is provided for engagement with the collar 225 provided on the nozzle. The airflow restrictor preferably comprises a flexible foam material having enough flexibility to adapt itself to fit tightly over the engagement collar 225.

Figure 19:
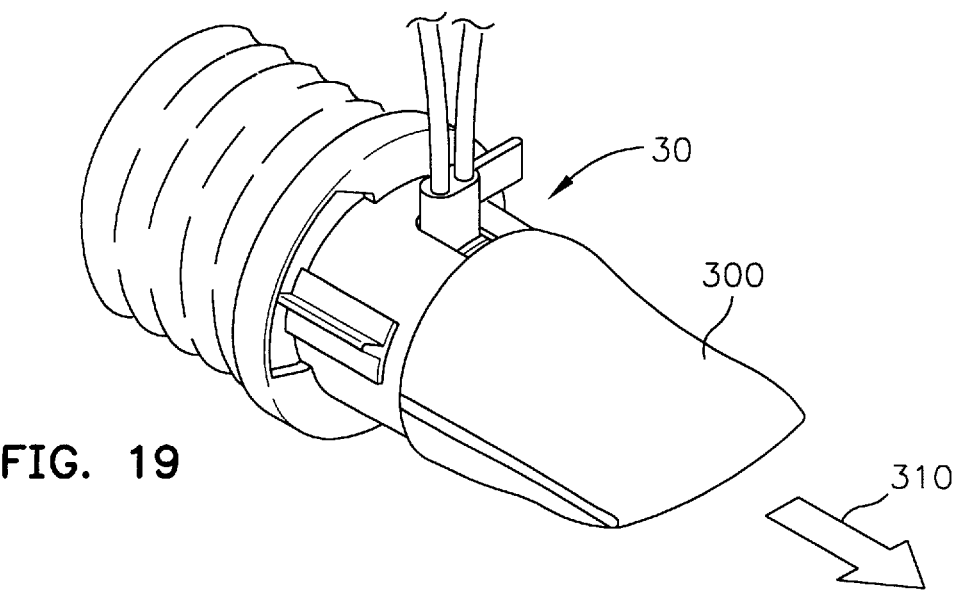
FIG. 19 is a perspective view of the airflow restrictor positioned over the outer cylindrical housing on the nozzle.

FIG. 19 is a perspective view of an airflow restrictor 300 positioned over the collar 225 on the nozzle. In this position an exemplary airflow, illustrated by 310, is restricted to a smaller amount than if it were unobstructed. As a result, the airflow restrictor 300 supplies sufficient backflow pressure for effective heating in the absence of a thermal blanket. If a patient thermal warming blanket is unavailable or its use is unnecessary, an airflow restrictor can be attached to the air hose in which the coil is disposed to provide enough resistance for fluid warming to take place. Preferably, the airflow restrictor is constructed of a non-woven/porous filter-like material adhesively attached to a cardboard or similar backing material and has a flattened conical shape designed to restrict airflow, although other materials and shapes would also be suitable.

The warming apparatus described herein has numerous advantages. The support unit stabilizes the helically coiled tube assembly securely in a fixed position within the air hose. An IV fluid heater according to this embodiment is easy to use, and as a result, it reduces the requisite amount of clinician training time; particularly, the single tube design allows the clinician to prime the apparatus straightforwardly in a manner similar to conventional IV tubes and lines. Further, even if air were to be inadvertently introduced into the system, the air will self-purge. The amount of IV fluid that must be passed through the tube in order to clear all air from the tube (the priming volume) is significantly reduced.

In addition, there are some cost advantages over the fluid warmer of the incorporation application, including a reduction in the overall length of tubing required over the manifold-multiple tube design. Furthermore, the use of a single tube coiled perpendicular to the airflow eliminates the need for tube spacers and the numerous bonds required by the multi-tube design of the first embodiment.

Advantageously, the warming tube assembly can be shifted between the first, open configuration and the second, collapsed configuration. In the open configuration, the coil is situated perpendicular to the airflow and thermal energy is efficiently transferred from the flowing heated gas to the IV fluid. In the second, collapsed position, the substantially flattened structure facilitates insertion into, and removal from, the air hose. The collapsed configuration reduces the thickness of the unit for packaging, shipping and storage. Furthermore, the collapsed configuration also reduces the tendency of the warming loop coils to kink during sterilization or shipping.

One may also contemplate other arrangements for engagement between the support structure and nozzle which will achieve the important objective of keeping the support structure in the air hose. It is also within the spirit of the invention to have the support structure engage and seat in the air hose, as long as it is kept by the engagement in the warmed air stream.

Referring to FIGS. 1, 6, 11, 13, 14, and 15 a method will be described for attaching the fluid warming apparatus 10 to the airflow restrictor 300 or, as appropriate, to the patient warming blanket 15 which has the inlet 35 for receiving the collar 225 and the airflow coupler 30. First, the inlet clamp 61 and the outlet clamp 68 are clamped to prevent entry of air into the heating tube that comprises the inlet segment 60, the coiled warming segment 63, and the outlet segment 67. After closing the clamps 61 and 68, the cap, provided on the inlet tube coupler 55 for shipping, should then be removed. The inlet segment 60 can then be attached, via the coupler 55, to the IV tube 13. Next, a cap provided on the end of the outlet tube coupler 70 for shipping should then be removed. Subsequently, the structure including the inlet segment 60, the coiled segment 63, and the outlet segment 67 should be pointed upward, in a position opposing gravitational force. Next, the clamps 61 and 68 are opened, allowing a flow of IV fluid 12 through the inlet segment 60, through the coiled segment 63, and out the outlet tube 67. The clinician should then verify that all air has been purged from the entire warming tube, and the procedure should be continued until accomplished. Subsequently, the clamps 61 and 68 should again be placed in a closed position. The outlet segment 67 may then be connected to a patient, taking appropriate measures to ensure that no air has been entrapped. Next, the coiled tube assembly 100 is inserted into the heated air conduit 20 and locked into the position illustrated in FIG. 15.

If an airflow restrictor is to be used, then it is inserted over the collar 225. However, if a warming blanket is to be utilized, then the nozzle 30 is placed into the inlet port 35 of the inflatable thermal blanket by conventional insertion techniques. Any additional extension tubing (not shown) may be tucked into available folds of the inflatable thermal blanket, thus ensuring that no heat will be lost from the warmed fluid. After these steps are completed, the pressurized, warmed airflow from the source 18 can be applied through the flexible air hose 20, thus quickly warming the IV fluids flowing therethrough and also inflating the thermal blanket (if utilized) to prevent patient hypothermia. The temperature of the warmed IV fluid can be constantly monitored for the patient's safety by using the temperature sensor 75.

Three embodiments of the present invention have been described for convectively warming intravenously administered fluids in a quick and safe manner. However, it should be understood that modifications and adaption thereof may occur to persons skilled in the art and therefore, protection afforded the present invention should only be limited in accordance with the scope of the claims.

FIGS. 20–23 illustrate several embodiments of a temperature indicator that include a thermochromic sensor. These embodiments show specific implementation of the temperature indicator 17 in FIGS. 1 and 2, and the temperature indicator 75 in FIG. 6.

Figure 20:
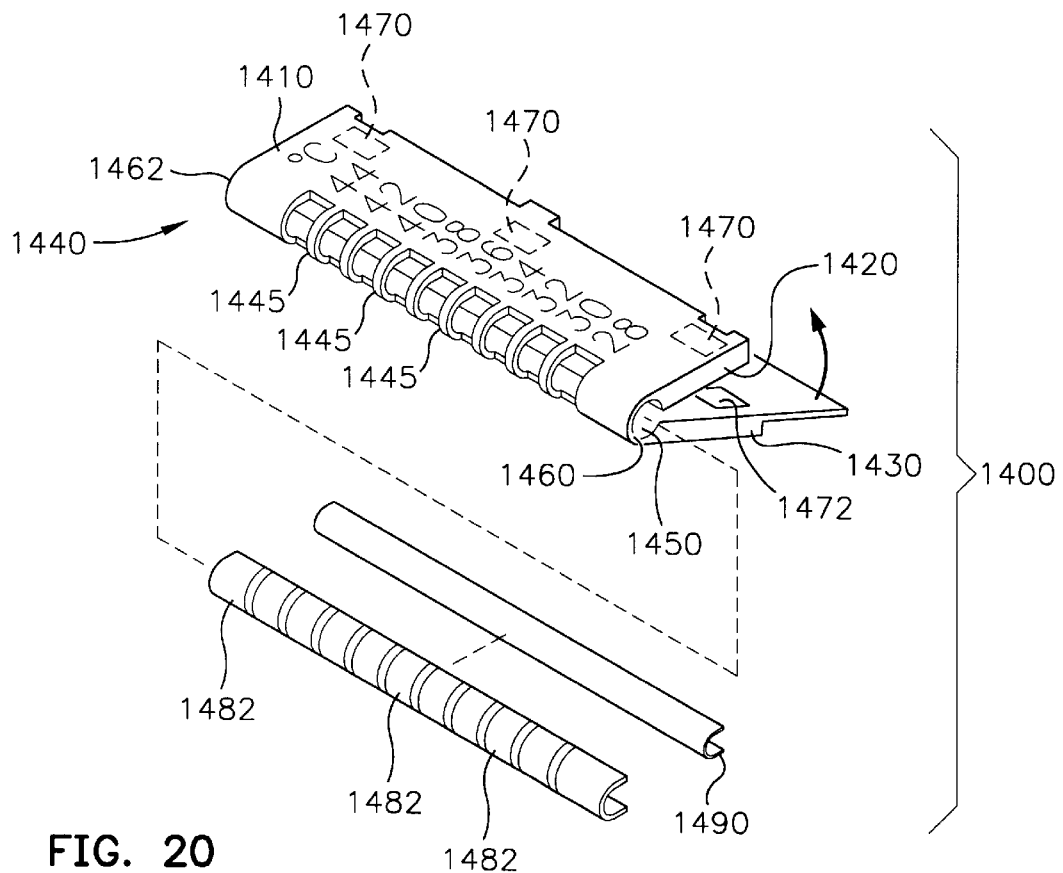
FIG. 20 is an exploded perspective view of a first temperature indicator.
Figure 21:
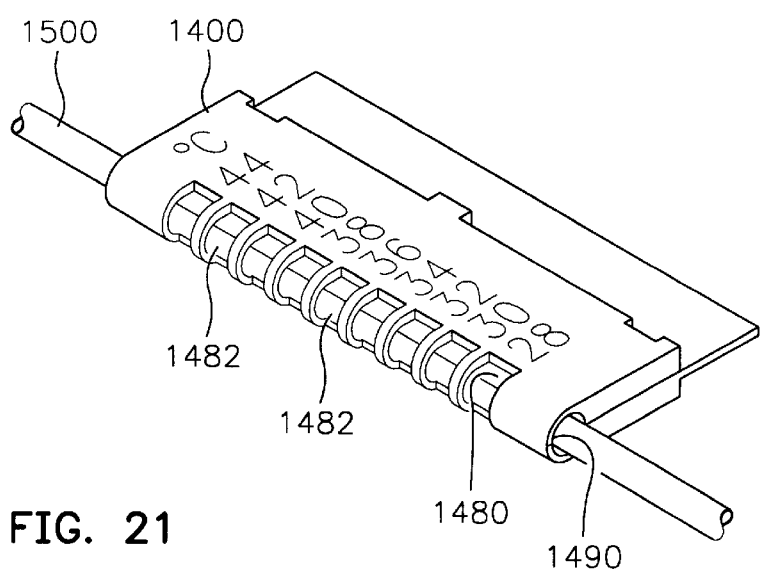
FIG. 21 is a perspective view of the first temperature indicator coupled to the outlet segment of the warming apparatus.

Reference is made to FIGS. 20 and 21, which illustrate the preferred embodiment of a temperature indicator illustrated generally at 1400. A hinged housing 1410 comprises a first side 1420, a second side 1430, and a hinge 1440 that connects the first and second sides. The hinge 1440 includes a plurality of flexible ribs 1445 connected between the first and second sides. The interior of the hinge defines an approximately cylindrical shape 1450 that extends longitudinally from a first end 1460 to second end 1462. The first side includes a plurality of hooks 1470 extending downwardly, and receiving notches 1472 are formed in the second side 1430.

A flexible thermochromic strip 1480 comprising a plurality of temperature responsive regions 1482 is longitudinally curled into an approximate U-shape. Typically, the thermochromic strips are manufactured flat, however, their flexibility, particularly at the hinge 1440 allows them to be longitudinally curled as illustrated in FIG. 20.

In order to ensure accurate temperature readings, a thermally conductive material 1490 is connected to the interior section of the thermochromic strip 1480. Preferably the thermally conductive material comprises a heat conducting metal such as aluminum, brass or copper. To construct the thermal sensor, the thermally conductive material 1490 is adhesively connected to the interior of the flexible thermochromic strip of 1480 and inserted within the cylindrical interior of the hinge 1440 of the hinged housing.

Reference is now made to FIG. 21 which is a perspective view of a temperature indicator 1400 affixed to a piece of conventional tubing 1500. Preferably, the tubing 1500 is cylindrical and is utilized to transfer heated IV fluid from a heating apparatus to a patient. In the fixed configuration of FIG. 21, the hooks 1470 shown in FIG. 20 are clasped into the receiving notches 1472 provided in the second side. The thermally conductive material 1490 evenly, efficiently and quickly transfers thermal energy to the thermochromic strip 1480. The visually responsive areas of the thermochromic strip 1482 of the thermochromic strip 1480 are viewable through the gaps provided between the ribs 1445 in the hinge 1440, for the purposes of viewing the temperature sensed by the thermochromic strip. The resulting structure is a lightweight, efficient, easily manufactured tool for measuring the temperature of IV fluid flowing through an IV tube. A series of numbers positioned on the first side provide a scale to indicate the temperature in Celsius. A similar scale on the second side indicates the temperature in Fahrenheit.

Figure 22:
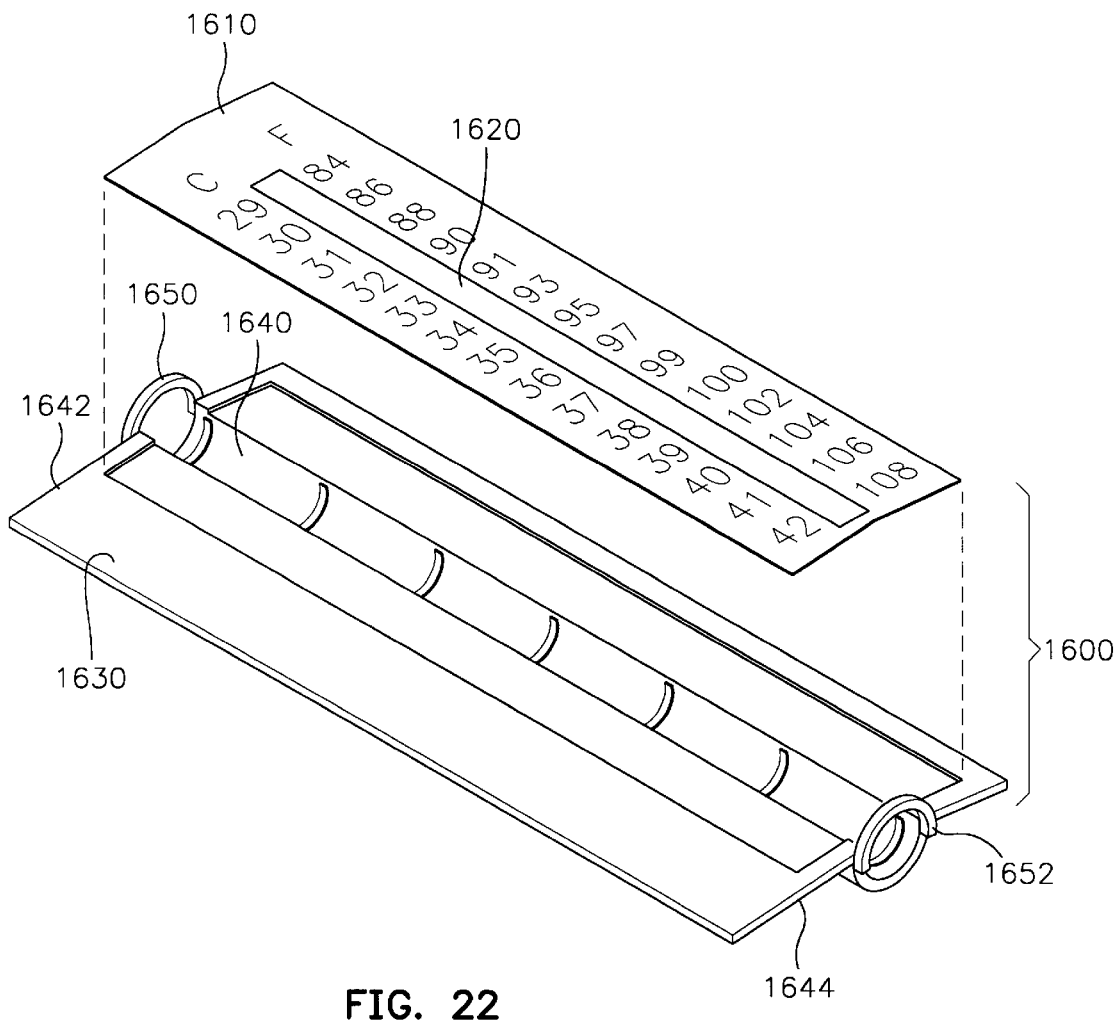
FIG. 22 is a perspective view of the first temperature indicator showing the indicator opened and partly disassembled.

FIG. 22 is an exploded view of an alternative embodiment of a temperature indicator 1600 that includes thermochromic sensor unit. A thermochromic sensor 1610 comprising a conventional thermochromic material includes a visually responsive area 1620 indicative of the temperature, and a plurality of scales that indicate the temperature corresponding to a visually indicated temperature. A tube housing 1630 comprises a plastic material including a half-pipe section 1640 that extends longitudinally from a first end 1642 to a second end 1644. A semi-circular tube retaining structure 1650 on the first end of the half-pipe 1640 is provided to hold the tube in position on the first end, and a second semi-circular support structure 1652 is provided on the second end of the half-pipe 1640 to hold the tube in position on the second end. In one method, the tube (not shown) is passed from the first end through the half-pipe 1640 and out the second end, and subsequently the thermochromic strip 1610 is adhesively positioned thereon, preferably tightly. In another embodiment, the thermochromic strip could be adhesively positioned before the tube is inserted through the half-pipe 1640.

Figure 23:
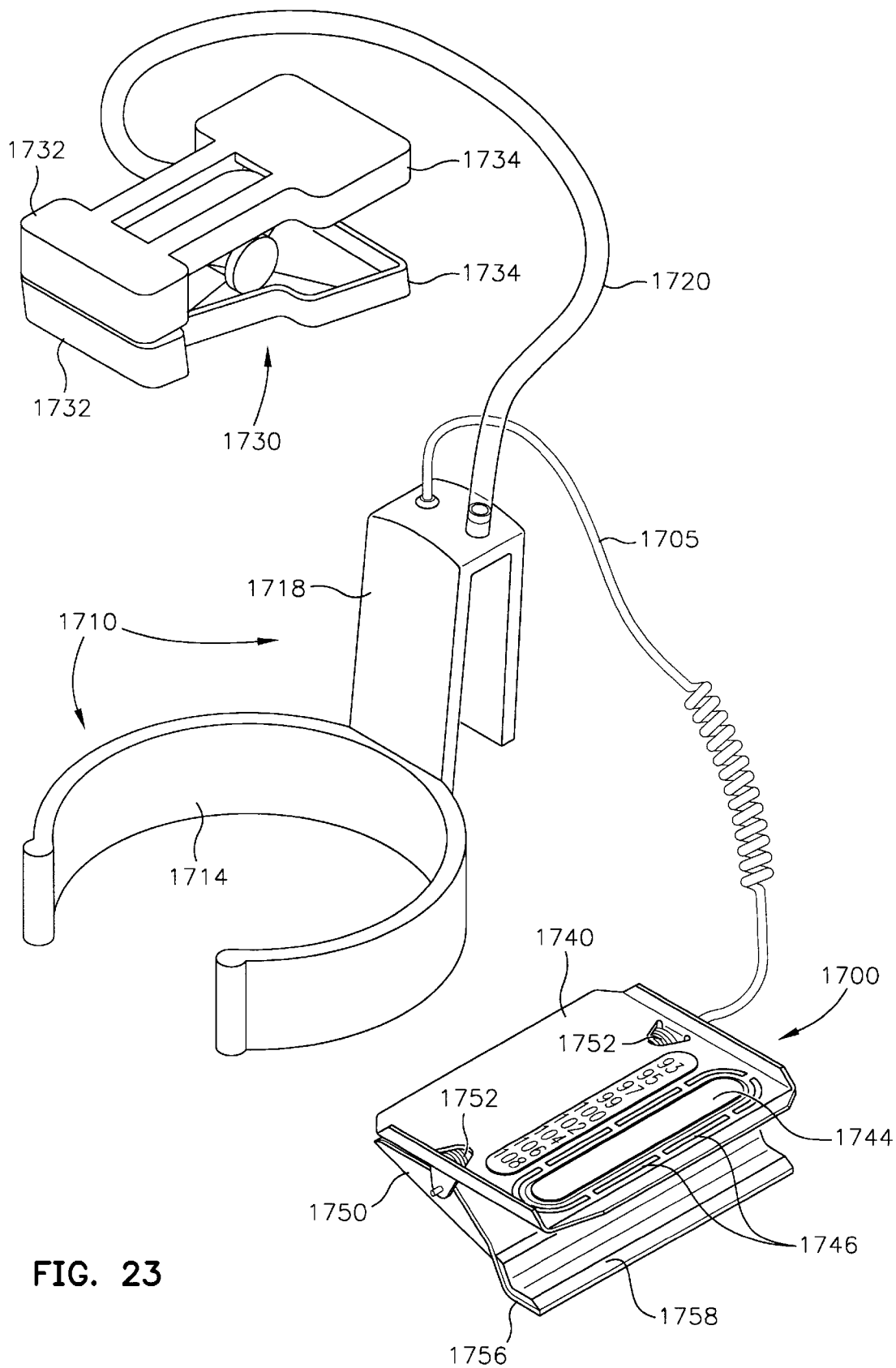
FIG. 23 is a perspective view of a second temperature indicator attached to a clamp that engages an air conduit.

Reference is now made to FIG. 23 which is a perspective view of still another alternative embodiment of a thermochromic sensor affixed to a clip structure, and also including a hose clamp and a notebook clip. Particularly, the alternative embodiment, illustrated generally at 1700 is coupled by a flexible cord 1705 to a hose clamp illustrated generally at 1710 including a semi-circular shaped clamping section 1714 having a shape for coupling onto a conventional air hose such as that illustrated at 20 in FIG. 1. Connected to the semi-circular shaped structure 1714 is a handle structure 1718 to which the flexible cord 1705 is attached. A flexible tube 1720 is also connected to the handle 1718. The other end of the tube 1720 is coupled to a conventional note holding clip 1730 including a pair of jaws 1732 and a pair of pressing surfaces 1734 to allow the jaws 1732 to open and hold, for example notes or other documents therein. Such a configuration could be useful to keep records of the temperature and other useful information.

Returning now to the alternative embodiment 1700 of the thermochromic sensor, a clip structure is provided that includes a first side 1740 onto which a thermochromic sensor 1744 has been installed. A plurality of gaps 1746 surround the thermochromic sensor 1744 in order to substantially reduce thermal flow from the thermochromic sensor 1744. The first side 1740 is preferably made of a rigid metal material. A scale is provided adjacent to the thermochromic sensor 1744 in order to provide an accurate reading of the temperature indicated thereby.

A second side 1750 of the clip is also preferably formed of a metal material. The first side is coupled to the second side by a conventional spring configuration 1752. The second side comprises, along the surface opposing the thermochromic sensor 1744, a longitudinally formed U-shaped section 1756, upon which a thermally insulative material 1758 has been adhesively connected. In operation, the U-shaped section 1756 operates together with the insulative and compressive material 1758 to hold a tube (not shown) tightly against the thermochromic sensor 1744, which then indicates the temperature of the tube. One advantage of the configuration of FIG. 23 is that it is rugged and durable, and can withstand many uses. However, it may have higher cost than the other embodiments.

We claim:

1. An apparatus for warming IV fluids with a warmed airflow during delivery from an IV fluid source to a patient, comprising;
   an air hose for connection to a source of warmed air at a first end and including a nozzle at a second end;
   an inlet tube segment for connection to said IV fluid source;
   an outlet tube segment for transporting said IV fluid;
   at least one helically coiled warming tube segment in fluid communication with said inlet tube segment and said outlet tube segment;
   at least a portion of the at least one helically coiled warming tube segment kept within said air hose; and
   means acting between the air hose and the at least one helically coiled warming tube segment for keeping the at least one helically coiled warming tube segment within the air hose.

2. The apparatus of claim 1, the means including:
   a support unit connected to the nozzle for supporting the at least one helically coiled warming tube segment in a helical configuration within the air hose.

3. The apparatus of claim 2, wherein said support unit comprises first and second elongated rib elements that extend substantially from one end of the helical configuration to the other end of said helical configuration.

4. The apparatus of claim 3, wherein each of said rib elements comprise a series of clasps spaced for affixing said at least one helically coiled warming tube segment.

5. The apparatus of claim 3, wherein said rib elements comprise plastic.

6. The apparatus of claim 3, wherein said rib elements are positioned substantially parallel to each other and are respectively attached on opposing sides of the helical configuration.

7. The apparatus of claim 6, further including a transverse member connecting said rib elements to each other.

8. The apparatus of claim 7, further comprising a first hinge connecting said first rib with said transverse member and a second hinge connecting said second rib with said transverse member.

9. The apparatus of claim 8, wherein the said first and second hinges allow transitioning from a first open configuration to a second, substantially collapsed configuration in which said rib elements are substantially in contact with each other.

10. The apparatus of claim 9, wherein said at least one helically coiled warming tubing segment includes multiple coils that define said helical configuration in said first open configuration and a substantially flattened configuration in said second, substantially collapsed configuration.

11. The apparatus of claim 1, further comprising an inflatable thermal blanket connected to the nozzle and a heater-blower unit connected to the first end of the air hose.

12. An apparatus for warming an IV fluid during delivery of the IV fluid to a patient, comprising:
    a source of IV fluid;
    a source of a warmed airstream;
    an air hose in communication with said warmed airstream source at a first end and including a nozzle at a second end;
    an inlet tube segment connected to said IV fluid source;
    an outlet tube segment for transporting said IV fluid;
    at least one warming tube segment configured in a substantially helical coil and connected to said inlet tube segment and said outlet tube segment and at least partially disposed in said air hose; and
    means acting between the air hose and the at least one warming tube segment for keeping the at least one warming tube segment in the air hose.

13. The apparatus of claim 12, wherein the means include engagement means, the apparatus further including an outer housing and an inner member slidably positioned within said outer housing, said outer housing having an outer slot and said inner member having an inner slot that, in a first configuration, allows insertion of said engagement means, and in a second configuration retains said engagement means on the nozzle.

14. The apparatus of claim 12, wherein the nozzle includes:
    an outer housing having a cylindrical shape and an outer slot formed longitudinally therein for allowing for insertion of the inlet tube segment and the outlet tube segment; and
    a locking mechanism including an inner cylindrical member slidably positioned within said outer housing, said inner cylindrical member including an inner slot for said inlet and outlet tube segments and a locking tab adjacent thereto for holding said inlet and outlet tube segments in position.

15. The apparatus of claim 14, wherein the inner cylindrical member comprises a lever to allow slidable rotation of the inner cylindrical member within the outer housing.

16. A fluid heating apparatus using a warmed air stream that is supplied through an air hose to warm an IV fluid supplied from an IV fluid source, comprising:
    at least one helically coiled tube;
    means engaged to the at least one helically coiled tube for keeping at least a portion of the at least one helically coiled tube in an air hose; and
    inlet and outlet IV tubes in fluid communication with the at least one helically coiled tube.

17. The fluid heating apparatus of claim 16, further including a means for supporting the at least one helically coiled tube in an air hose.

18. The fluid heating apparatus of claim 17 wherein the means for supporting comprises:
    a support unit for insertion into an air hose, said support unit having a first rib, a second rib substantially parallel to said first rib, and a transverse member hingably connected on one end to said first rib and on the other end to said second rib so that said support unit has at least two configurations including a first configuration in which the first and second ribs are spaced apart and a second configuration in which the first and second ribs are closely positioned;

said at least one helically coiled tube comprising a flexible tube helically supported on said first and second ribs such that in said first configuration said segment is substantially longitudinally aligned within said air hose, and in said second configuration said segment has an approximately flattened shape.

19. The fluid heating apparatus of claim 18 wherein said first and second ribs comprise a plurality of clasps for holding said flexible tube in a helically coiled configuration.

20. The fluid heating apparatus of claim 18 wherein the plurality of clasps are formed on the outside edge of the first and second ribs.

21. The fluid heating apparatus of claim 18 wherein said first and second ribs comprise a semirigid plastic.

22. The fluid heating apparatus of claim 18 wherein said first rib, said second rib, and said transverse member comprise a single piece of plastic.

23. The fluid heating apparatus of claim 18 wherein said support unit further comprises an insertion member extending from said transverse member for engaging an air hose nozzle.

24. The fluid heating apparatus of claim 23 wherein said flexible tube further includes an inlet segment, an outlet segment, and said at least one helically coiled tube is situated between said inlet and outlet segments, said insertion member including a retaining clip with a first hole in which the inlet segment is disposed and a second hole in which the outlet segment is disposed.

25. The fluid heating apparatus of claim 18 further comprising an insertion lever including a retaining clip extending from said transverse member having an extended shape for rotation of said transverse member to move said support unit between said first and second configurations.

* * * * *